United States Patent
Dillon et al.

(10) Patent No.: US 7,776,872 B2
(45) Date of Patent: *Aug. 17, 2010

(54) DIAMINOPYRIMIDINES AS P2X₃ AND P2X₂/₃ MODULATORS

(75) Inventors: Michael Patrick Dillon, San Francisco, CA (US); Alam Jahangir, San Jose, CA (US); Alfred Sui-Ting Lui, Sunnyvale, CA (US); Robert Stephen Wilhelm, Los Altos, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 867 days.

This patent is subject to a terminal disclaimer.

(21) Appl. No.: 11/510,015

(22) Filed: Aug. 25, 2006

(65) Prior Publication Data

US 2007/0049610 A1     Mar. 1, 2007

Related U.S. Application Data

(60) Provisional application No. 60/713,243, filed on Sep. 1, 2005.

(51) Int. Cl.
  C07D 239/48   (2006.01)
  C07D 401/12   (2006.01)
  A61K 31/506   (2006.01)
(52) U.S. Cl. ............... 514/272; 514/275; 544/298; 544/324; 544/325
(58) Field of Classification Search ............ 544/298, 544/324, 325; 514/272, 275
See application file for complete search history.

(56) References Cited

U.S. PATENT DOCUMENTS

| | | | |
|---|---|---|---|
| 2,953,567 A | 9/1960 | Hitchings et al. | |
| 3,715,357 A | 2/1973 | Rey-Bellet et al. | |
| 3,849,470 A | 11/1974 | Cresswell et al. | |
| 3,850,927 A | 11/1974 | Cresswell et al. | |
| 3,852,276 A | 12/1974 | Cresswell et al. | |
| 3,855,265 A | 12/1974 | Cresswell et al. | |
| 3,931,181 A | 1/1976 | Kompis et al. | |
| 3,940,393 A | 2/1976 | Greenspan et al. | |
| 3,991,050 A | 11/1976 | Cresswell et al. | |
| 4,024,145 A | 5/1977 | Kompis | |
| 4,033,962 A | 7/1977 | Rosen | |
| 4,039,543 A | 8/1977 | Kompis et al. | |
| 4,052,553 A | 10/1977 | Cresswell et al. | |
| 4,075,209 A | 2/1978 | Jernow et al. | |
| 4,108,888 A | 8/1978 | Rosen | |
| 4,115,650 A | 9/1978 | Manchand | |
| 4,143,227 A | 3/1979 | Rosen | |
| 4,144,263 A | 3/1979 | Yeowell et al. | |
| 4,151,196 A | 4/1979 | Rosen | |
| 4,216,319 A | 8/1980 | Yeowell et al. | |
| 4,232,023 A | 11/1980 | Dick et al. | |
| 4,255,574 A | 3/1981 | Rosen | |
| 4,258,045 A | 3/1981 | Poe et al. | |
| 4,386,084 A | 5/1983 | Scharwaechter et al. | |
| 4,415,574 A | 11/1983 | Laruelle et al. | |
| 4,485,248 A | 11/1984 | Dall'Asta | |
| 4,515,948 A | 5/1985 | Kompis et al. | |
| 4,587,341 A | 5/1986 | Roth et al. | |
| 4,587,342 A * | 5/1986 | Daluge et al. | ............... 544/324 |
| 4,590,271 A | 5/1986 | Daluge et al. | |
| 4,883,798 A | 11/1989 | Petöcz et al. | |
| 4,912,112 A | 3/1990 | Seydel et al. | |
| 4,996,198 A | 2/1991 | Schildknecht et al. | |
| 5,063,219 A | 11/1991 | Schildknecht et al. | |
| 5,240,640 A | 8/1993 | Siiman et al. | |
| 5,258,373 A | 11/1993 | Schildknecht et al. | |
| 5,541,186 A | 7/1996 | Breu et al. | |
| 6,136,971 A | 10/2000 | Harrington et al. | |
| 6,211,185 B1 | 4/2001 | Strobel et al. | |
| 6,410,543 B1 | 6/2002 | Strobel et al. | |
| 6,423,720 B1 | 7/2002 | Gangjee | |
| 6,583,148 B1 | 6/2003 | Kelley et al. | |
| 2003/0040513 A1 | 2/2003 | Baxter et al. | |

FOREIGN PATENT DOCUMENTS

| | | |
|---|---|---|
| EP | 0 237 516 A1 | 9/1987 |
| EP | 0 658 548 B1 | 11/1997 |
| EP | 0 959 073 A1 | 11/1999 |
| EP | 0 743 307 B1 | 9/2001 |
| EP | 0 959 072 B1 | 9/2002 |
| EP | 1 310 493 A1 | 5/2003 |
| WO | WO 01/17976 A1 | 3/2001 |

(Continued)

OTHER PUBLICATIONS

Barnes, Frontrunners in novel pharmacotherapy of COPD, Current Opinion in Pharmacology, 2008, 8:300-307.*

(Continued)

*Primary Examiner*—Deepak Rao
(74) *Attorney, Agent, or Firm*—Robert C. Hall

(57) ABSTRACT

Compounds of the formula I:

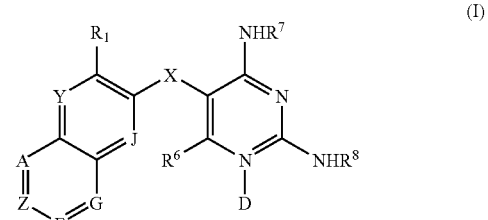

or pharmaceutically acceptable salts thereof, wherein A, D, E, G, J, X, Y, Z R⁶, R⁷ and R⁸ are as defined herein. Also provided are methods of using the compounds for treating diseases mediated by a $P2X_3$ and/or a $P2X_{2/3}$ receptor antagonist and methods of making the compounds.

10 Claims, No Drawings

FOREIGN PATENT DOCUMENTS

| | | |
|---|---|---|
| WO | WO 01/22938 A1 | 4/2001 |
| WO | WO 01/81335 A1 | 11/2001 |
| WO | WO 01/81338 A1 | 11/2001 |
| WO | WO 02/08200 A2 | 1/2002 |
| WO | WO 02/24665 A1 | 3/2002 |
| WO | WO 02/053557 A1 | 7/2002 |
| WO | WO 02/083650 A1 | 10/2002 |
| WO | WO 02/094767 A2 | 11/2002 |
| WO | WO 03/063794 A2 | 8/2003 |

OTHER PUBLICATIONS

Cazzola et al., Treating Systemic effects of COPD, TRENDS in Pharmacological Sciences, vol. 28, No. 10, pp. 544-550, 2007.*

Fox et al., Models of chronic obstructive pulmonary disease: a review of current status, Drug Discovery Today: Disease Models, vol. 1, No. 3, pp. 319-328 (2004).*

Calas, M., et al., "Synthesis of new trimethoprim analogs. Antibacterial structure-activity relationship," *Eur. J. Med. Chem*, 1982 17(6): 497-504.

Selassie, C.D., et al., "Quantitative structure-activity relationships of 2,4-diamino-5-(2-x-benzyl) pyrimidines versus bacterial and avian dihydrofolate reductase," *J. Med. Chemistry*, 1998 41(22): 4261-4272.

Dunn, S.M.J., et al., "Kinetics of ternary complex formation between dihydrofolate reductase, coenzyme, and inhibitors," *Biochemistry*, 1980, 19: 766-773.

Falco, E.A., et al., "5-Arylthiopyrimidines. 1. 2,4-diamino derivatives," *Journal of Organic Chemistry*, 1961, 26: 1143-1146.

Seiler, P., et al., "Partition coefficients of 5-(substituted benzyl)-2,4-diaminopyrimidines," *Arzneim.-Forsch*, 1982, 32 (7): 711-714.

* cited by examiner

DIAMINOPYRIMIDINES AS P2X$_3$ AND P2X$_{2/3}$ MODULATORS

CROSS REFERENCE TO RELATED APPLICATIONS

This application is entitled to the benefit of provisional patent application Ser. No. 60/713,243 filed on Sep. 1, 2005, the disclosure of which is incorporated herein by reference.

FIELD OF THE INVENTION

This invention pertains to compounds useful for treatment of diseases associated with P2X purinergic receptors, and more particularly to P2X$_3$ and/or P2X$_{2/3}$ antagonists usable for treatment of genitourinary, pain, gastrointestinal and respiratory diseases, conditions and disorders.

BACKGROUND OF THE INVENTION

The urinary bladder is responsible for two important physiological functions: urine storage and urine emptying. This process involves two main steps: (1) the bladder fills progressively until the tension in its walls rises above a threshold level; and (2) a nervous reflex, called the micturition reflex, occurs that empties the bladder or, if this fails, at least causes a conscious desire to urinate. Although the micturition reflex is an autonomic spinal cord reflex, it can also be inhibited or mediated by centers in the cerebral cortex or brain.

Purines, acting via extracellular purinoreceptors, have been implicated as having a variety of physiological and pathological roles. (See, Burnstock (1993) Drug Dev. Res. 28:195-206.) ATP, and to a lesser extent, adenosine, can stimulate sensory nerve endings resulting in intense pain and a pronounced increase in sensory nerve discharge. ATP receptors have been classified into two major families, the P2Y- and P2X-purinoreceptors, on the basis of molecular structure, transduction mechanisms, and pharmacological characterization. The P2Y-purinoreceptors are G-protein coupled receptors, while the P2X-purinoreceptors are a family of ATP-gated cation channels. Purinergic receptors, in particular, P2X receptors, are known to form homomultimers or heteromultimers. To date, cDNAs for several P2X receptors subtypes have been cloned, including: six homomeric receptors, P2X$_1$; P2X$_2$; P2X$_3$; P2X$_4$; P2X$_5$; and P2X$_7$; and three heteromeric receptors P2X$_{2/3}$, P2X$_{4/6}$, P2X$_{1/5}$ (See, e.g., Chen, et al. (1995) Nature 377:428-431; Lewis, et al. (1995) Nature 377:432-435; and Burnstock (1997) Neurophamacol. 36:1127-1139). The structure and chromosomal mapping of mouse genomic P2X$_3$ receptor subunit has also been described (Souslova, et al. (1997) Gene 195:101-111). In vitro, co-expression of P2X$_2$ and P2X$_3$ receptor subunits is necessary to produce ATP-gated currents with the properties seen in some sensory neurons (Lewis, et al. (1995) Nature 377:432-435).

P2X receptor subunits are found on afferents in rodent and human bladder urothelium. Data exists suggesting that ATP may be released from epithelial/endothelial cells of the urinary bladder or other hollow organs as a result of distention (Burnstock (1999) J. Anatomy 194:335-342; and Ferguson et al. (1997) J. Physiol. 505:503-511). ATP released in this manner may serve a role in conveying information to sensory neurons located in subepithelial components, e.g., suburothelial lamina propria (Namasivayam, et al. (1999) BJU Intl. 84:854-860). The P2X receptors have been studied in a number of neurons, including sensory, sympathetic, parasympathetic, mesenteric, and central neurons (Zhong, et al. (1998) Br. J. Pharmacol. 125:771-781). These studies indicate that purinergic receptors play a role in afferent neurotransmission from the bladder, and that modulators of P2X receptors are potentially useful in the treatment of bladder disorders and other genitourinary diseases or conditions.

Recent evidence also suggests a role of endogenous ATP and purinergic receptors in nociceptive responses in mice (Tsuda, et al. (1999) Br. J. Pharmacol. 128:1497-1504). ATP-induced activation of P2X receptors on dorsal root ganglion nerve terminals in the spinal cord has been shown to stimulate release of glutamate, a key neurotransmitter involved in nociceptive signaling (Gu and MacDermott, Nature 389:749-753 (1997)). P2X$_3$ receptors have been identified on nociceptive neurons in the tooth pulp (Cook et al., Nature 387:505-508 (1997)). ATP released from damaged cells may thus lead to pain by activating P2X$_3$ and/or P2X$_{2/3}$ containing receptors on nociceptive sensory nerve endings. This is consistent with the induction of pain by intradermally applied ATP in the human blister-base model (Bleehen, Br J Pharmacol 62:573-577 (1978)). P2X antagonists have been shown to be analgesic in animal models (Driessen and Starke, Naunyn Schmiedebergs Arch Pharmacol 350:618-625 (1994)). This evidence suggests that P2X$_2$ and P2X$_3$ are involved in nociception, and that modulators of P2X receptors are potentially useful as analgesics.

Other researchers have shown that P2X$_3$ receptors are expressed in human colon, and are expressed at higher levels in inflamed colon than in normal colon (Y. Yiangou et al, Neurogastroenterol Mot (2001)13:365-69). Other researchers have implicated the P2X$_3$ receptor in detection of distension or intraluminal pressure in the intestine, and initiation of reflex contractions (X. Bian et al., J Physiol (2003) 551.1: 309-22), and have linked this to colitis (G. Wynn et al., Am J Physiol Gastrointest Liver Physiol (2004) 287:G647-57).

Inge Brouns et al. (Am J Respir Cell Mol Biol (2000) 23:52-61) found that P2X$_3$ receptors are expressed in pulmonary neuroepithelial bodies (NEBs), implicating the receptor in pain transmission in the lung. More recently, others have implicated P2X$_2$ and P2X$_3$ receptors in pO$_2$ detection in pulmonary NEBs (W. Rong et al., J Neurosci (2003) 23(36): 11315-21).

There is accordingly a need for methods of treating diseases, conditions and disorders mediated by P2X$_3$ and/or P2X$_{2/3}$ receptors, as well as a need for compounds that act as modulators of P2X receptors, including antagonists of P2X$_3$ and P2X$_{2/3}$ receptors. The present invention satisfies these needs as well as others.

SUMMARY OF THE INVENTION

The invention provides compounds of the formula (I):

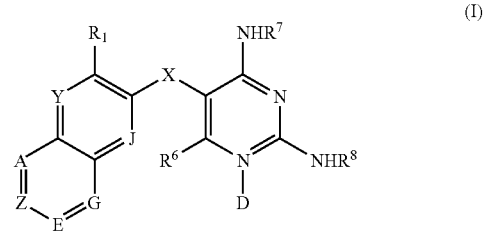

or a pharmaceutically acceptable salt thereof, wherein:

X is:
—$CH_2$—;
—O—;
—$S(O)_n$—;
or —$NR^c$—
wherein
n is from 0 to 2 and
$R^c$ is hydrogen or alkyl;

D is an optional oxygen;

one or two of A, E, G, J, Y and Z are N while the others are $CR^a$; or A, E, G, J, Y and Z are $CR^a$;

$R^1$ is:
alkyl;
alkenyl;
alkynyl;
cycloalkyl;
cycloalkenyl;
halo;
haloalkyl; or
hydroxyalkyl;

each $R^a$ is independently:
hydrogen;
alkyl;
alkenyl;
amino;
aminosulfonyl;
halo;
amido;
haloalkyl;
alkoxy;
hydroxy;
haloalkoxy;
nitro; amino;
hydroxyalkyl;
alkoxyalkyl;
hydroxyalkoxy;
alkynylalkoxy;
alkylsulfonyl;
arylsulfonyl;
cyano;
aryl;
heteroaryl;
heterocyclyl;
heterocyclylalkoxy;
aryloxy;
heteroaryloxy;
aralkyloxy;
heteroaralkyloxy;
optionally substituted phenoxy;
—C≡C—$R^b$—;
—$(CH_2)_m$—$(Z)_n$—(CO)—$R^c$;
—$(CH_2)_m$—$(Z)_n$—$SO_2$—$(NR^d)_n$—$R^c$;
wherein
m and n each independently is 0 or 1,
Z is O or $NR^d$,
$R^b$ is hydrogen; alkyl; aryl; aralkyl; heteroaryl; heteroaralkyl; hydroxyalkyl; alkoxyalkyl; alkylsulfonylalkyl; aminoalkyl; cyanoalkyl; alkylsilyl; cycloalkyl; cycloalkylalkyl; heterocycl; and heterocyclylalkyl;
$R^c$ is hydrogen, alkyl, hydroxy, alkoxy, amino, hydroxyalkyl or alkoxyalkyl, and
each $R^d$ is independently hydrogen or alkyl;

$R^6$ is:
hydrogen;
alkyl;
halo;
haloalkyl;
amino; or
alkoxy;

$R^7$ and $R^8$ each independently is:
hydrogen;
alkyl;
cycloalkyl;
cycloalkylalkyl;
haloalkyl;
haloalkoxy;
hydroxyalky;
alkoxyalkyl;
alkylsulfonyl;
alkylsulfonylalkyl;
aminocarbonyloxyalkyl;
hydroxycarbonylalkyl;
hydroxyalkyloxycarbonylalkyl;
aryl;
aralkyl;
arylsulfonyl;
heteroaryl;
heteroarylalkyl;
heteroarylsulfonyl;
heterocyclyl;
heterocyclylalkyl; or
—(C=O)—$R^e$;
wherein
$R^e$ is alkyl, alkoxy, cycloalkyl, cycloalkoxy, cycloalkylalkyl, cycloalkylalkoxy, aryl, aryloxy, heteroaryl, heteroaryloxy, aralkyl, aralkoxy, heteroaralkyl, heteroaralkoxy, —$(CH_2)_p$—C(=O)—$R^f$, —(CH=CH)—C(=O)—$R^f$, or —CH($NH_2$)—$R^g$
wherein
$R^f$ is hydrogen, hydroxy, alkyl, alkoxy, cycloalkyl, cycloalkoxy, cycloalkylalkyl, cycloalkylalkoxy, aryl, aryloxy, heteroaryl, heteroaryloxy, aralkyl, aralkoxy, heteroaralkyl, heteroaralkoxy, or amino;
p is 2 or 3;
$R^g$ is hydrogen, alkyl, hydroxyalkyl, aminoalkyl, optionally substituted phenyl, benzyl, guanidinylalkyl, carboxyalkyl, amidoalkyl, thioalkyl or imidazolalkyl.

The invention also provides and pharmaceutical compositions comprising the compounds, methods of using the compounds, and methods of preparing the compounds.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an", and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e.

$C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —R'—R", where R' is oxo and R" is alkyl as defined herein.

"Alkylsulfonyl" means a moiety of the formula —R'—R", where R' is —$SO_2$— and R" is alkyl as defined herein.

"Alkylsulfonylalkyl means a moiety of the formula —R'—R"–R''' where where R' is alkylene, R" is —$SO_2$- and R''' is alkyl as defined herein.

"Alkylamino means a moiety of the formula —NR—R' wherein R is hyrdogen or alkyl and R' is alkyl as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Aminosulfonyl" means a group —$SO_2$—NR'R" wherein R and R" each indepently is hydrogen or alkyl.

"Alkylsulfonylamido" means a moiety of the formula —NR'$SO_2$—R wherein R is alkyl and R' is hydrogen or alkyl.

"Aminocarbonyloxyalkyl" or "carbamylalkyl" means a group of the formula —R—O—C(O)—NR'R" wherein R is alkylene and R', R" each independently is hydrogen or alkyl as defined herein.

"Alkynylalkoxy" means a group of the formula —O—R—R' wherein R is alkylene and R' is alkynyl as defined herein.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Arylalkyl" and "Aralkyl", which may be used interchangeably, mean a radical—$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Arylalkyl" means a group of the formula —R—R' wherein R is alkylene and R' is aryl as defined herein.

"Arylsulfonyl means a group of the formula —$SO_2$—R wherein R is aryl as defined herein.

"Aryloxy" means a group of the formula —O—R wherein R is aryl as defined herein.

"Aralkyloxy" means a group of the formula —O—R—R" wherein R is alkylene and R' is aryl as defined herein.

"Cyanoalkyl" means a moiety of the formula —R'—R", where R' is alkylene as defined herein and R" is cyano or nitrile.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" means a moiety of the formula —R'—R", where R' is alkylene and R" is cycloalkyl as defined herein.

"Heteroalkyl" means an alkyl radical as defined herein wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

"Heteroarylalkyl" or "heteroaralkyl" means a group of the formula —R—R' wherein R is alkylene and R' is heteroaryl as defined herein.

"Heteroarylsulfonyl means a group of the formula —SO$_2$—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"Urea" or "ureido" means a group of the formula —NR'—C(O)—NR"R''' wherein R', R" and R''' each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —SO$_2$—NR'R" wherein R', R" and R''' each independently is hydrogen or alkyl.

"Optionally substituted", when used in association with "aryl", phenyl", "heteroaryl" "cycloalkyl" or "heterocyclyl", means an aryl, phenyl, heteroaryl, cyclohexyl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is alkyl, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl).

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Disorders of the urinary tract" or "uropathy" used interchangeably with "symptoms of the urinary tract" means the pathologic changes in the urinary tract. Examples of urinary tract disorders include, but are not limited to, incontinence, benign prostatic hypertrophy (BPH), prostatitis, detrusor hyperreflexia, outlet obstruction, urinary frequency, nocturia, urinary urgency, overactive bladder, pelvic hypersensitivity, urge incontinence, urethritis, prostatodynia, cystitis, idiophatic bladder hypersensitivity, and the like.

"Disease states associated with the urinary tract" or "urinary tract disease states" or "uropathy" used interchangeably with "symptoms of the urinary tract" mean the pathologic changes in the urinary tract, or dysfunction of urinary bladder smooth muscle or its innervation causing disordered urinary storage or voiding. Symptoms of the urinary tract include, but are not limited to, overactive bladder (also known as detrusor hyperactivity), outlet obstruction, outlet insufficiency, and pelvic hypersensitivity.

"Overactive bladder" or "detrusor hyperactivity" includes, but is not limited to, the changes symptomatically manifested as urgency, frequency, altered bladder capacity, incontinence, micturition threshold, unstable bladder contractions, sphincteric spasticity, detrusor hyperreflexia (neurogenic bladder), detrusor instability, and the like.

"Outlet obstruction" includes, but is not limited to, benign prostatic hypertrophy (BPH), urethral stricture disease, tumors, low flow rates, difficulty in initiating urination, urgency, suprapubic pain, and the like.

"Outlet insufficiency" includes, but is not limited to, urethral hypermobility, intrinsic sphincteric deficiency, mixed incontinence, stress incontinence, and the like.

"Pelvic Hypersensitivity" includes, but is not limited to, pelvic pain, interstitial (cell) cystitis, prostatodynia, prostatitis, vulvadynia, urethritis, orchidalgia, overactive bladder, and the like.

"Respiratory disorder" refers to, without limitation, chronic obstructive pulmonary disease (COPD), asthma, bronchospasm, and the like.

"Gastrointestinal disorder" ("GI disorder") refers to, without limitation, Irritable Bowel Syndrome (IBS), Inflammatory Bowel Disease (IBD), biliary colic and other biliary disorders, renal colic, diarrhea-dominant IBS, pain associated with GI distension, and the like.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

All patents and publications identified herein are incorporated herein by reference in their entirety.

COMPOUNDS OF THE INVENTION

The invention provides compounds of the formula I:

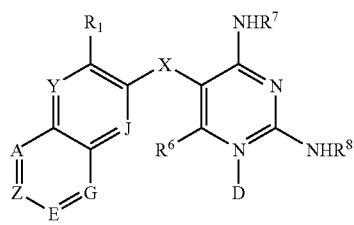

(I)

or a pharmaceutically acceptable salt thereof, wherein:

X is:
—$CH_2$—;
—O—;
—$S(O)_n$—;
or —$NR^c$—
wherein
n is from 0 to 2 and
$R^c$ is hydrogen or alkyl;

D is an optional oxygen;

one or two of A, E, G, J, Y and Z are N while the others are $CR^a$; or A, E, G, J, Y and Z are $CR^a$;

$R^1$ is:
alkyl;
alkenyl;
alkynyl;
cycloalkyl;
cycloalkenyl;
halo;
haloalkyl; or
hydroxyalkyl;

each $R^a$ is independently:
hydrogen;
alkyl;
alkenyl;
amino;
aminosulfonyl;
halo;
amido;
haloalkyl;
alkoxy;
hydroxy;
haloalkoxy;
nitro; amino;
hydroxyalkyl;
alkoxyalkyl;
hydroxyalkoxy;
alkynylalkoxy;
alkylsulfonyl;
arylsulfonyl;
cyano;
aryl;
heteroaryl;
heterocyclyl;
heterocyclylalkoxy;
aryloxy;
heteroaryloxy;
aralkyloxy;
heteroaralkyloxy;
optionally substituted phenoxy;
—C≡C—$R^b$—;
—$(CH_2)_m$—$(Z)_n$—(CO)—$R^c$;
—$(CH_2)_m$—$(Z)_n$—$SO_2$—$(NR^d)_n$—$R^c$;
wherein
m and n each independently is 0 or 1,
Z is O or $NR^d$,
$R^b$ is hydrogen; alkyl; aryl; aralkyl; heteroaryl; heteroaralkyl; hydroxyalkyl; alkoxyalkyl; alkylsulfonylalkyl; aminoalkyl; cyanoalkyl; alkylsilyl, cycloalkyl, cycloalkylalkyl; heterocycl; and heterocyclylalkyl;
$R^c$ is hydrogen, alkyl, hydroxy, alkoxy, amino, hydroxyalkyl or alkoxyalkyl, and
each $R^d$ is independently hydrogen or alkyl;

$R^6$ is:
- hydrogen;
- alkyl;
- halo;
- haloalkyl;
- amino; or
- alkoxy;

$R^7$ and $R^8$ each independently is:
- hydrogen;
- alkyl;
- cycloalkyl;
- cycloalkylalkyl;
- haloalkyl;
- haloalkoxy;
- hydroxyalky;
- alkoxyalkyl;
- alkylsulfonyl;
- alkylsulfonylalkyl;
- aminocarbonyloxyalkyl;
- hydroxycarbonylalkyl;
- hydroxyalkyloxycarbonylalkyl;
- aryl;
- aralkyl;
- arylsulfonyl;
- heteroaryl;
- heteroarylalkyl;
- heteroarylsulfonyl;
- heterocyclyl;
- heterocyclylalkyl; or
- —(C═O)—$R^e$;

wherein
  $R^e$ is alkyl, alkoxy, cycloalkyl, cycloalkoxy, cycloalkylalkyl, cycloalkylalkoxy, aryl, aryloxy, heteroaryl, heteroaryloxy, aralkyl, aralkoxy, heteroaralkyl, heteroaralkoxy, —(CH$_2$)$_p$—C(═O)—$R^f$, —(CH═CH)—C(═O)—$R^f$, or —CH(NH$_2$)—$R^g$
  wherein
    $R^f$ is hydrogen, hydroxy, alkyl, alkoxy, cycloalkyl, cycloalkoxy, cycloalkylalkyl, cycloalkylalkoxy, aryl, aryloxy, heteroaryl, heteroaryloxy, aralkyl, aralkoxy, heteroaralkyl, heteroaralkoxy, or amino;
    p is 2 or 3;
    $R^g$ is hydrogen, alkyl, hydroxyalkyl, aminoalkyl, optionally substituted phenyl, benzyl, guanidinylalkyl, carboxyalkyl, amidoalkyl, thioalkyl or imidazolalkyl.

In many embodiments of formula I, X is —O— or —CH$_2$—.

In many embodiments of formula I, D is absent.

In certain embodiments of formula I, $R^1$ is ethyl, isopropyl, iodo, ethynyl or cyclopropyl. In such embodiments $R^1$ may be isopropyl, iodo or ethynyl.

In certain embodiments of formula I, $R^5$ and $R^6$ are hydrogen.

In certain embodiments of formula I, $R^2$ is hydrogen.

In certain embodiments of formula I, each $R^a$ is independently is hydrogen, alkyl, alkenyl, halo, haloalkyl, alkoxy, hydroxy, haloalkoxy, alkylsulfonyl, heteroaryl, cyano, or —C≡C—$R^a$.

In certain embodiments of formula I, each $R^a$ is independently is hydrogen, alkyl, halo, alkoxy, hydroxy, haloalkoxy, heteroaryl, alkylsulfonyl or —C≡C—$R^b$.

In certain embodiments of formula I, each $R^a$ is independently is hydrogen, alkyl or alkoxy.

In certain embodiments of formula I, $R^7$ and $R^8$ are hydrogen.

In certain embodiments of formula I, one of $R^7$ and $R^8$ is hydrogen and the other is alkyl, hydroxyalkyl or haloalkyl.

In certain embodiments of formula I, one of $R^7$ and $R^8$ is hydrogen and the other is hydrogen, alkyl, cycloalkyl, cycloalkylalkyl, haloalkyl, hydroxyalky; or alkoxyalkyl.

In certain embodiments of formula I, X is O or —CH$_2$—, $R^1$ is ethyl, isopropyl, iodo, ethynyl or cyclopropyl and $R^2$, $R^3$, $R^4$ and $R^a$ are hydrogen, methyl or methoxy.

In certain embodiments of formula I, X is O or —CH$_2$—, $R^1$ is ethyl, isopropyl, iodo, ethynyl or cyclopropyl, $R^2$, $R^3$, $R^4$ and $R^a$ are hydrogen, methyl or methoxy, and $R^7$ and $R^8$ are hydrogen.

In certain embodiments of formula I, X is O or —CH$_2$—, $R^1$ is isopropyl, or iodo, $R^2$, $R^3$, $R^4$ and $R^a$ are hydrogen, methyl or methoxy, and $R^7$ and $R^8$ are hydrogen.

In certain embodiments of formula I, X is O or —CH$_2$—, $R^1$ is isopropyl, or iodo, $R^2$, $R^3$, $R^4$ and $R^a$ are hydrogen, methyl or methoxy, $R^7$ is hydrogen, and $R^8$ is hydroxyalkyl.

In certain embodiments of formula I, A, E, G, J, Y and Z are $CR^a$.

In certain embodiments of formula I, A, E, G, J, Y and Z are $CR^a$ and $R^a$ is hydrogen, alkyl, alkoxy, hydroxy, halo, haloalkyl or haloalkoxy.

In certain embodiments of formula I, A, E, G, J, and Y are $CR^a$ and Z is N.

In certain embodiments of formula I, A, E, G, J and Y are $CR^a$, Z is N and $R^a$ is hydrogen, alkyl, alkoxy, hydroxy, halo, haloalkyl or haloalkoxy.

In certain embodiments of formula I, Y is N and A, E, G, J and Z are $CR^a$.

In certain embodiments of formula I, Y is N, A, E, G, J and Z are $CR^a$, and $R^a$ is hydrogen, alkyl, alkoxy, hydroxy, halo, haloalkyl or haloalkoxy.

In certain embodiments of formula I, Y and Z are N and A, E, G and J are $CR^a$.

In certain embodiments of formula I, A is N and E, G, J, Y and Z are $CR^a$.

In certain embodiments of formula I, E is N and A, Z, G, J and Y are $CR^a$.

In certain embodiments of formula I, G is N and A, Z, E, J and Y are $CR^a$.

In certain embodiments of formula I, A and E are N and Z, G, J and Y are $CR^a$.

In certain embodiments of formula I, Z and G are N and A, E, J and Y are $CR^a$.

In certain embodiments of formula I, A and G are N and E, Z, J and Y are $CR^a$.

In certain embodiments of formula I, one of Y and Z is N and A, E, G, J and the other of Y and Z are $CR^a$.

In certain embodiments of formula I, Y and A are N and Z, E, J and G are $CR^a$.

In certain embodiments of formula I, Y and E are N and Z, A, J and G are $CR^a$.

In certain embodiments of formula I, Y and G are N and A, E, J and Z are $CR^a$.

In certain embodiments of formula I, A, E, G, J, Y and Z are $CR^a$, X is O, $R^1$ is isopropyl or iodo, $R^2$, $R^3$, $R^4$ and $R^a$ are hydrogen, and $R^7$ and $R^8$ are hydrogen.

In certain embodiments of formula I, A, E, G, J, Y and Z are $CR^a$, X is O, $R^1$ is isopropyl or iodo, $R^2$, $R^3$, $R^4$ and $R^a$ are hydrogen, one of $R^7$ and $R^8$ is hydrogen, and the other is alkyl, hydroxyalkyl or haloalkyl, preferably hydroxyalkyl.

In certain embodiments of formula I, A, E, G, J, Y and Z are $CR^a$, X is O, $R^1$ is isopropyl or iodo, $R^2$, $R^3$, $R^4$ and $R^a$ are hydrogen, $R^7$ is hydrogen, and $R^8$ is alkyl, hydroxyalkyl or haloalkyl, preferably hydroxyalkyl.

In certain embodiments of formula I, A, E, G, J, Y and Z are $CR^a$, X is O, $R^1$ is isopropyl or iodo, $R^2$, $R^3$, $R^4$ and $R^a$ are hydrogen, $R^8$ is hydrogen, and $R^7$ is alkyl, hydroxyalkyl or haloalkyl, preferably hydroxyalkyl.

In certain embodiments of formula I, Y is N, A, E, G, J, and Z are $CR^a$, X is O, $R^1$ is isopropyl or iodo, $R^2$, $R^3$, $R^4$ and $R^a$ are hydrogen, and $R^7$ and $R^8$ are hydrogen.

In certain embodiments of formula I, Y is N, A, E, G, J, and Z are $CR^a$, X is O, $R^1$ is isopropyl or iodo, $R^2$, $R^3$, $R^4$ and $R^a$ are hydrogen, one of $R^7$ and $R^8$ is hydrogen, and the other is alkyl, hydroxyalkyl or haloalkyl, preferably hydroxyalkyl.

In certain embodiments of formula I, Y is N, A, E, G, J, and Z are $CR^a$, X is O, $R^1$ is isopropyl or iodo, $R^2$, $R^3$, $R^4$ and $R^a$ are hydrogen, $R^7$ is hydrogen, and $R^8$ is alkyl, hydroxyalkyl or haloalkyl, preferably hydroxyalkyl.

In certain embodiments of formula I, Y is N, A, E, G, J, and Z are $CR^a$, X is O, $R^1$ is isopropyl or iodo, $R^2$, $R^3$, $R^4$ and $R^a$ are hydrogen, $R^8$ is hydrogen, and $R^7$ is alkyl, hydroxyalkyl or haloalkyl, preferably hydroxyalkyl.

In certain embodiments of formula I, A is N, E, G, J, Y and Z are $CR^a$, X is O, $R^1$ is isopropyl or iodo, $R^2$, $R^3$, $R^4$ and $R^a$ are hydrogen, and $R^7$ and $R^8$ are hydrogen.

In certain embodiments of formula I, A is N, E, G, J, Y and Z are $CR^a$, X is O, $R^1$ is isopropyl or iodo, $R^2$, $R^3$, $R^4$ and $R^a$ are hydrogen, one of $R^7$ and $R^8$ is hydrogen, and the other is alkyl, hydroxyalkyl or haloalkyl, preferably hydroxyalkyl.

In certain embodiments of formula I, A is N, E, G, J, Y and Z are $CR^a$, X is O, $R^1$ is isopropyl or iodo, $R^2$, $R^3$, $R^4$ and $R^a$ are hydrogen, $R^7$ is hydrogen, and $R^8$ is alkyl, hydroxyalkyl or haloalkyl, preferably hydroxyalkyl.

In certain embodiments of formula I, A is N, E, G, J, Y and Z are $CR^a$, X is O, $R^1$ is isopropyl or iodo, $R^2$, $R^3$, $R^4$ and $R^a$ are hydrogen, $R^8$ is hydrogen, and $R^7$ is alkyl, hydroxyalkyl or haloalkyl, preferably hydroxyalkyl.

In certain embodiments of formula I, A, E, G, J, Y and Z are $CR^a$, X is O, $R^1$ is isopropyl or iodo, $R^2$, $R^3$ and $R^4$ are hydrogen, $R^a$ is hydrogen or methyl, and $R^7$ and $R^8$ are hydrogen.

In certain embodiments of formula I, A, E, G, J, Y and Z are $CR^a$, X is O, $R^1$ is isopropyl or iodo, $R^2$, $R^3$ and $R^4$ are hydrogen, $R^a$ is hydrogen or methyl, one of $R^7$ and $R^8$ is hydrogen, and the other is alkyl, hydroxyalkyl or haloalkyl, preferably hydroxyalkyl.

In certain embodiments of formula I, A, E, G, J, Y and Z are $CR^a$, X is O, $R^1$ is isopropyl or iodo, $R^2$, $R^3$ and $R^4$ are hydrogen, $R^a$ is hydrogen or methyl, $R^7$ is hydrogen, and $R^8$ is alkyl, hydroxyalkyl or haloalkyl, preferably hydroxyalkyl.

In certain embodiments of formula I, A, E, G, J, Y and Z are $CR^a$, X is O, $R^1$ is isopropyl or iodo, $R^2$, $R^3$ and $R^4$ are hydrogen, $R^a$ is hydrogen or methyl, $R^8$ is hydrogen, and $R^7$ is alkyl, hydroxyalkyl or haloalkyl, preferably hydroxyalkyl.

In embodiments of the invention where $R^7$ or $R^8$ is alkyl, preferred alkyl include methyl, ethyl, isopropyl, isobutyl, and 1-(ethyl)-propyl.

In embodiments of the invention where $R^7$ or $R^8$ is haloalkyl, preferred haloalkyl include trifluoromethyl and 2,2,2-trifluoroethyl.

In embodiments of the invention where $R^7$ or $R^8$ is hydroxyalkyl, preferred hydroxyalkyl include hydroxyethyl, 2-hydroxypropyl, 2-hydroxy-1-methyl-ethyl, 2-hydroxy-1-(hydroxymethyl)-ethyl and 3-hydroxypropyl.

In certain embodiments of the invention, the subject compounds are more specifically of formula II:

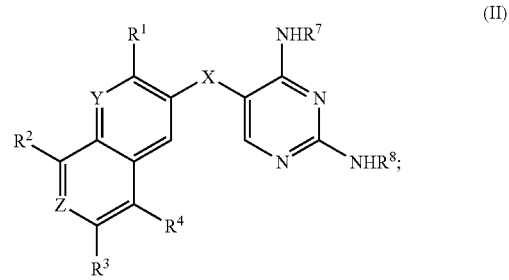

(II)

wherein:

$R^2$, $R^3$ and $R^4$ each independently is:
  hydrogen;
  alkyl;
  alkenyl;
  amino;
  halo;
  amido;
  haloalkyl;
  alkoxy;
  hydroxy;
  haloalkoxy;
  nitro; amino;
  hydroxyalkyl;
  alkoxyalkyl;
  hydroxyalkoxy;
  alkynylalkoxy;
  alkylsulfonyl;
  arylsulfonyl;
  cyano;
  aryl;
  heteroaryl;
  heterocyclyl;
  heterocyclylalkoxy;
  aryloxy;
  heteroaryloxy;
  aralkyloxy;
  heteroaralkyloxy;
  optionally substituted phenoxy;
  —C≡C—$R^b$—;
  —$(CH_2)_m$—$(Z)_n$—(CO)—$R^c$;
  —$(CH_2)_m$—$(Z)_n$—$SO_2$—$(NR^d)_n$—$R^c$
  wherein
  m and n each independently is 0 or 1,
  Z is O or $NR^d$,
  $R^b$ is hydrogen; alkyl; aryl; aralkyl; heteroaryl; heteroaralkyl; hydroxyalkyl; alkoxyalkyl; alkylsulfonylalkyl; aminoalkyl; cyanoalkyl; alkylsilyl; cycloalkyl, cycloalkylalkyl; heterocycl; and heterocyclylalkyl;
  $R^c$ is hydrogen, alkyl, hydroxy, alkoxy, amino, hydroxyalkyl or alkoxyalkyl;
  each $R^d$ is independently hydrogen or alkyl; and X, Y, Z, $R^1$, $R^7$ and $R^8$ are as defined herein.

In certain embodiments of the invention, the subject compounds are more specifically of formula III:

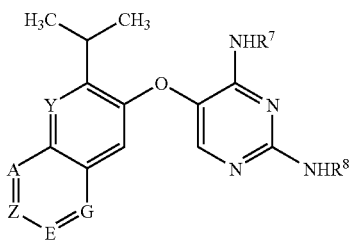
(III)

wherein A, E, G, Y, Z, $R^1$, $R^7$ and $R^8$ are as defined herein.

In certain embodiments of formula III, A, E, G, Y and Z are $CR^a$, $R^a$ is hydrogen, and $R^7$ and $R^8$ are hydrogen.

In certain embodiments of formula III, A, E, G, Y and Z are $CR^a$, $R^a$ is hydrogen, one of $R^7$ and $R^8$ is hydrogen, and the other is alkyl, hydroxyalkyl or haloalkyl, preferably hydroxyalkyl.

In certain embodiments of formula III, A, E, G, Y and Z are $CR^a$, $R^a$ is hydrogen, $R^7$ is hydrogen, and $R^8$ is alkyl, hydroxyalkyl or haloalkyl, preferably hydroxyalkyl.

In certain embodiments of formula III, A, E, G, Y and Z are $CR^a$, $R^a$ is hydrogen, $R^8$ is hydrogen, and $R^7$ is alkyl, hydroxyalkyl or haloalkyl, preferably hydroxyalkyl.

In certain embodiments of formula III, Y is N, A, E, G, Z are $CR^a$, $R^a$ is hydrogen, and $R^7$ and $R^8$ are hydrogen.

In certain embodiments of formula III, Y is N, A, E, G, Z are $CR^a$, $R^a$ is hydrogen, one of $R^7$ and $R^8$ is hydrogen, and the other is alkyl, hydroxyalkyl or haloalkyl, preferably hydroxyalkyl.

In certain embodiments of formula III, Y is N, A, E, G, Z are $CR^a$, $R^a$ is hydrogen, $R^7$ is hydrogen, and $R^8$ is alkyl, hydroxyalkyl or haloalkyl, preferably hydroxyalkyl.

In certain embodiments of formula III, Y is N, A, E, G, Z are $CR^a$, $R^a$ is hydrogen, $R^8$ is hydrogen, and $R^7$ is alkyl, hydroxyalkyl or haloalkyl, preferably hydroxyalkyl.

In certain embodiments of formula III, A is N, E, G, Y and Z are $CR^a$, $R^a$ is hydrogen, and $R^7$ and $R^8$ are hydrogen.

In certain embodiments of formula III, A is N, E, G, Y and Z are $CR^a$, $R^a$ is hydrogen, one of $R^7$ and $R^8$ is hydrogen, and the other is alkyl, hydroxyalkyl or haloalkyl, preferably hydroxyalkyl.

In certain embodiments of formula III, A is N, E, G, Y and Z are $CR^a$, $R^a$ is hydrogen, $R^7$ is hydrogen, and $R^8$ is alkyl, hydroxyalkyl or haloalkyl, preferably hydroxyalkyl.

In certain embodiments of formula III, A, E, G, Y and Z are $CR^a$, $R^a$ is hydrogen or methyl, and $R^7$ and $R^8$ are hydrogen.

In certain embodiments of formula III, A, E, G, Y and Z are $CR^a$, $R^a$ is hydrogen or methyl, one of $R^7$ and $R^8$ is hydrogen, and the other is alkyl, hydroxyalkyl or haloalkyl, preferably hydroxyalkyl.

In certain embodiments of formula III, A, E, G, Y and Z are $CR^a$, $R^a$ is hydrogen or methyl, $R^7$ is hydrogen, and $R^8$ is alkyl, hydroxyalkyl or haloalkyl, preferably hydroxyalkyl.

In certain embodiments of formula III, A, E, G, Y and Z are $CR^a$, $R^a$ is hydrogen or methyl, $R^8$ is hydrogen, and $R^7$ is alkyl, hydroxyalkyl or haloalkyl, preferably hydroxyalkyl.

In certain embodiments of the invention, the subject compounds are more specifically of formula IV:

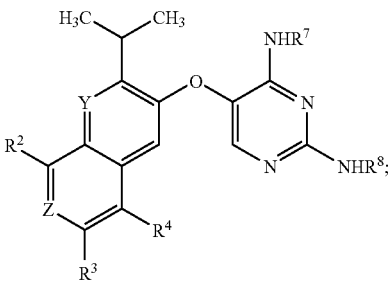
(IV)

wherein Y, Z, $R^2$, $R^3$, $R^4$, $R^7$ and $R^8$ are as defined herein.

In certain embodiments of the invention, the subject compounds are more specifically of formula V:

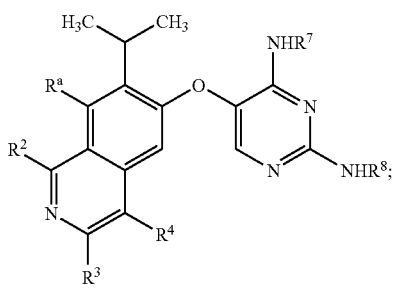
(V)

wherein $R^2$, $R^3$, $R^4$, $R^7$, $R^8$ and $R^a$ are as defined herein.

In certain embodiments of the invention, the subject compounds are more specifically of formula VI:

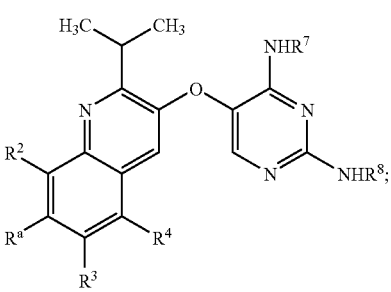
(VI)

wherein $R^2$, $R^3$, $R^4$, $R^7$, $R^8$ and $R^a$ are as defined herein.

In certain embodiments of the invention, the subject compounds are more specifically of formula VII:

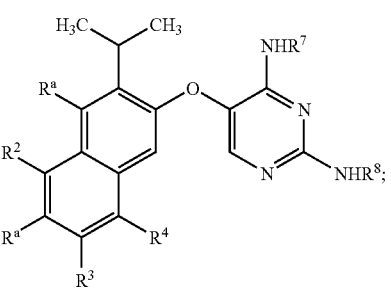
(VII)

wherein $R^2$, $R^3$, $R^4$, $R^7$, $R^8$ and $R^a$ are as defined herein.

In certain embodiments of the invention, the subject compounds are more specifically of formula VIII:

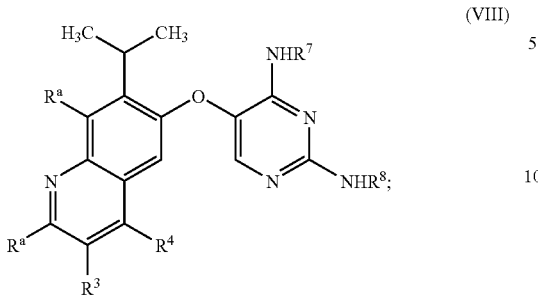

(VIII)

wherein $R^3$, $R^4$, $R^7$, $R^8$ and $R^a$ are as defined herein.

In certain embodiments of the invention, the subject compounds are more specifically of formula IX:

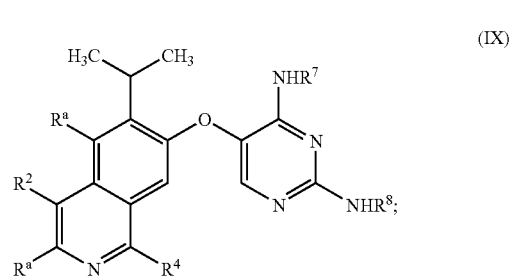

(IX)

wherein $R^2$, $R^4$, $R^7$, $R^8$ and $R^a$ are as defined herein.

In certain embodiments of the invention, the subject compounds are more specifically of formula X:

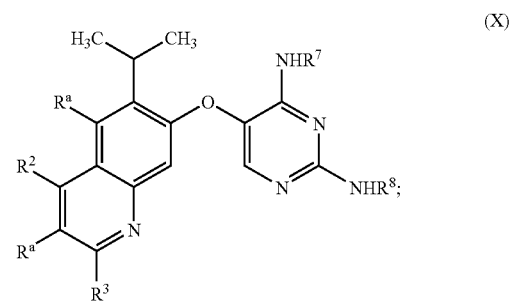

(X)

wherein $R^2$, $R^3$, $R^7$, $R^8$ and $R^a$ are as defined herein.

In certain embodiments of the invention, the subject compounds are more specifically of formula XI:

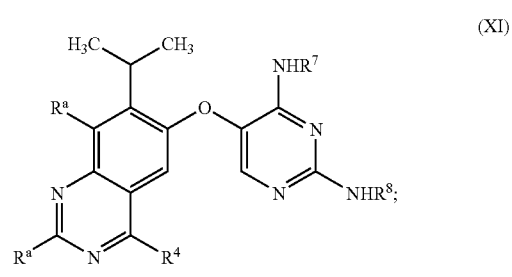

(XI)

wherein $R^4$, $R^7$, $R^8$ and $R^a$ are as defined herein.

In certain embodiments of the invention, the subject compounds are more specifically of formula XII:

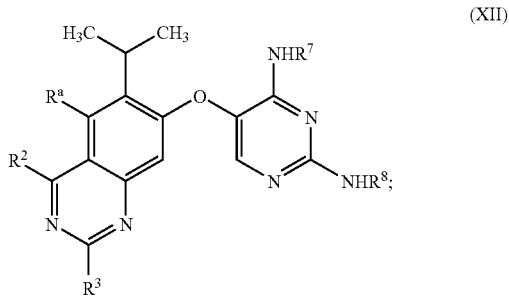

(XII)

wherein $R^3$, $R^7$, $R^8$ and $R^a$ are as defined herein.

In certain embodiments of the invention, the subject compounds are more specifically of formula XIII:

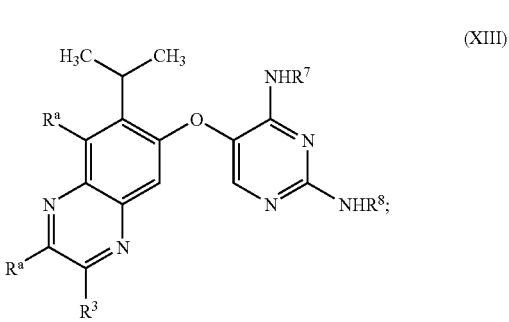

(XIII)

wherein $R^3$, $R^7$, $R^8$ and $R^a$ are as defined herein.

In certain embodiments of the invention, the subject compounds are more specifically of formula XIV:

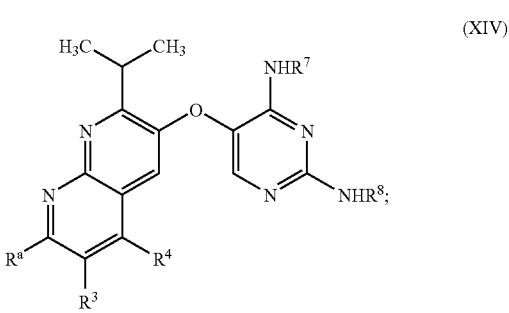

(XIV)

wherein $R^3$, $R^4$, $R^7$, $R^8$ and $R^a$ are as defined herein.

In certain embodiments of the invention, the subject compounds are more specifically of formula XV:

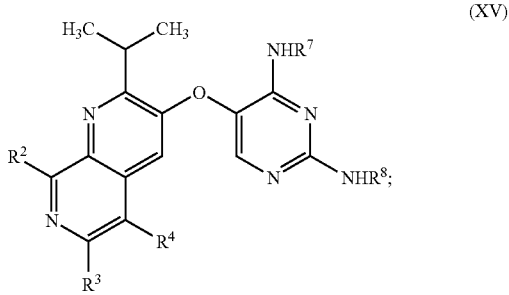

(XV)

wherein $R^2$, $R^3$, $R^4$, $R^7$, $R^8$ and $R^a$ are as defined herein.

In certain embodiments of the invention, the subject compounds are more specifically of formula XVI:

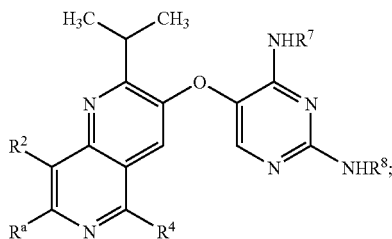

(XVI)

wherein $R^2$, $R^4$, $R^7$, $R^8$ and $R^a$ are as defined herein.

In certain embodiments of the invention, the subject compounds are more specifically of formula XVII:

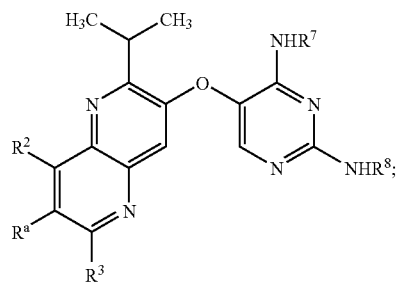

(XVII)

wherein $R^2$, $R^3$, $R^7$, $R^8$ and $R^a$ are as defined herein.

In certain embodiments of any of formulas IV through XVII, $R^2$, $R^3$ and $R^4$ are hydrogen.

In certain embodiments of any of formulas IV through XVII, $R^2$ is methyl and $R^3$ and $R^4$ are hydrogen.

In certain embodiments of any of formulas IV through XVII, $R^7$ and $R^8$ are hydrogen.

In certain embodiments of any of formulas IV through XVII, one of $R^7$ and $R^8$ is hydrogen, and the other is alkyl, hydroxyalkyl or haloalkyl, preferably hydroxyalkyl.

In certain embodiments of any of formulas IV through XVII, $R^7$ is hydrogen, and $R^8$ is alkyl, hydroxyalkyl or haloalkyl, preferably hydroxyalkyl.

In certain embodiments of any of formulas IV through XVII, $R^8$ is hydrogen, and $R^7$ is alkyl, hydroxyalkyl or haloalkyl, preferably hydroxyalkyl.

Where any of $R^1$, $R^2$, $R^3$, $R^4$, R, $R^6$, $R^7$, $R^8$, $R^a$, $R^b$, $R^c$, $R^d$, $R^e$, $R^f$, $R^g$, or $R^h$ is alkyl or contains an alkyl moiety, such alkyl is preferably lower alkyl, i.e. $C_1$-$C_6$alkyl, and more preferably $C_1$-$C_4$alkyl.

The invention also provides methods for treating a disease mediated by a $P2X_3$ receptor antagonist, a $P2X_{2/3}$ receptor antagonist, or both, the method comprising administering to a subject in need thereof an effective amount of a compound of any of formulas (I) through (VIII). The disease may be genitourinary disease or urinary tract disease. In other instances the disease may be a disease is associated with pain. The urinary tract disease may be: reduced bladder capacity; frequent micturition; urge incontinence; stress incontinence; bladder hyperreactivity; benign prostatic hypertrophy; prostatitis; detrusor hyperreflexia; urinary frequency; nocturia; urinary urgency; overactive bladder; pelvic hypersensitivity; urethritis; prostatitits; pelvic pain syndrome; prostatodynia; cystitis; or idiophatic bladder hypersensitivity. The disease associated with pain may be: inflammatory pain; surgical pain; visceral pain; dental pain; premenstrual pain; central pain; pain due to burns; migraine or cluster headaches; nerve injury; neuritis; neuralgias; poisoning; ischemic injury; interstitial cystitis; cancer pain; viral, parasitic or bacterial infection; post-traumatic injury; or pain associated with irritable bowel syndrome. The disease may be a respiratory disorder, such as chronic obstructive pulmonary disorder (COPD), asthma, or bronchospasm, or a gastrointestinal (GI) disorder such as Irritable Bowel Syndrome (IBS), Inflammatory Bowel Disease (IBD), biliary colic and other biliary disorders, renal colic, diarrhea-dominant IBS, pain associated with GI distension.

Representative compounds in accordance with the methods of the invention are shown in Table 1.

TABLE 1

| # | Structure | Name (Autonomp ™) | MP/M + H |
|---|-----------|-------------------|----------|
| 1 | ![structure] | 5(3-Isopropyl-8-methyl-naphthalen-2-yloxy)-pyrimidine-2,4-diamine | 180-182° C. |
| 2 | ![structure] | 5-(3-Isopropyl-5-methyl-naphthalen-2-yloxy)-pyrimidine-2,4-diamine | 148° C. |

TABLE 1-continued

| # | Structure | Name (Autonomp ™) | MP/M + H |
|---|---|---|---|
| 3 | 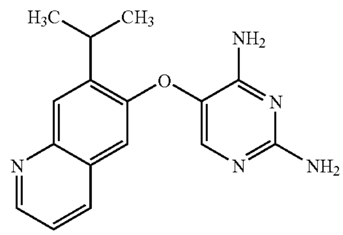 | 5-(7-Isopropyl-quinolin-6-yloxy)-pyrimidine-2,4-diamine | 206.9-208.2° C. |
| 4 | 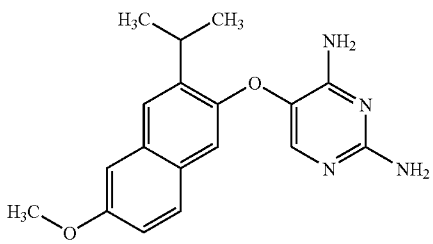 | 5-(3-Isopropyl-6-methoxy-naphthalen-2-yloxy)-pyrimidine-2,4-diamine | 170-172° C. |
| 5 | 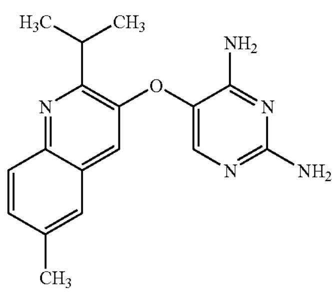 | 5-(2-Isopropyl-6-methyl-quinolin-3-yloxy)-pyrimidine-2,4-diamine | 239.4-242.1° C. |
| 6 | 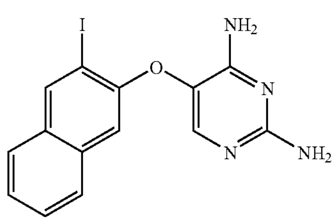 | 5-(3-Iodo-naphthalen-2-yloxy)-pyrimidine-2,4-diamine | 195-197° C. |
| 7 | 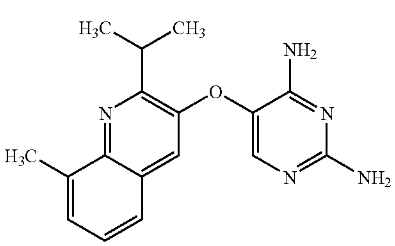 | 5-(2-Isopropyl-8-methyl-quinolin-3-yloxy)-pyrimidine-2,4-diamine | 248.3-249.4° C. |
| 8 | 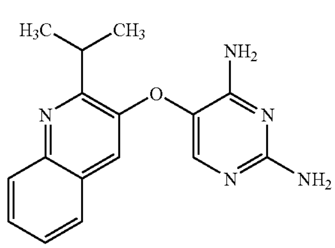 | 5-(2-Isopropyl-quinolin-3-yloxy)-pyrimidine-2,4-diamine | 285.0-285.6° C. |

TABLE 1-continued

| # | Structure | Name (Autonomp ™) | MP/M + H |
|---|---|---|---|
| 9 | 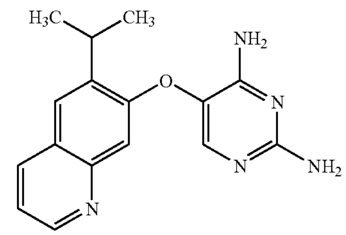 | 5-(6-Isopropyl-quinolin-7-yloxy)-pyrimidine-2,4-diamine | 276.3-278.° C.7 |
| 10 | 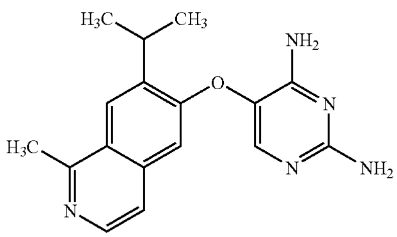 | 5-(7-Isopropyl-1-methyl-isoquinolin-6-yloxy)-pyrimidine-2,4-diamine | 242-244° C. |
| 11 | 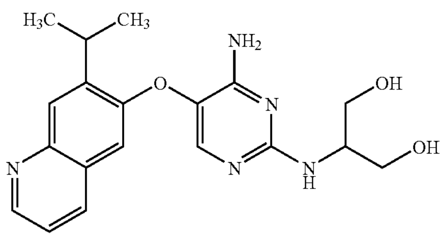 | 2-[4-Amino-5-(7-isopropyl-quinolin-6-yloxy)-pyrimidin-2-ylamino]-propane-1,3-diol | 171.9-174.4° C. |

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare specific compounds of formula (I) wherein L is a leaving group and $R^1$, $R^2$, $R^3$ and $R^4$ are as defined herein.

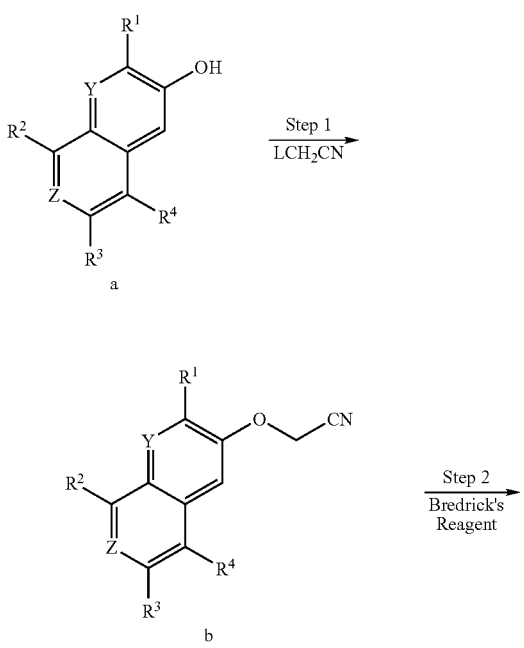

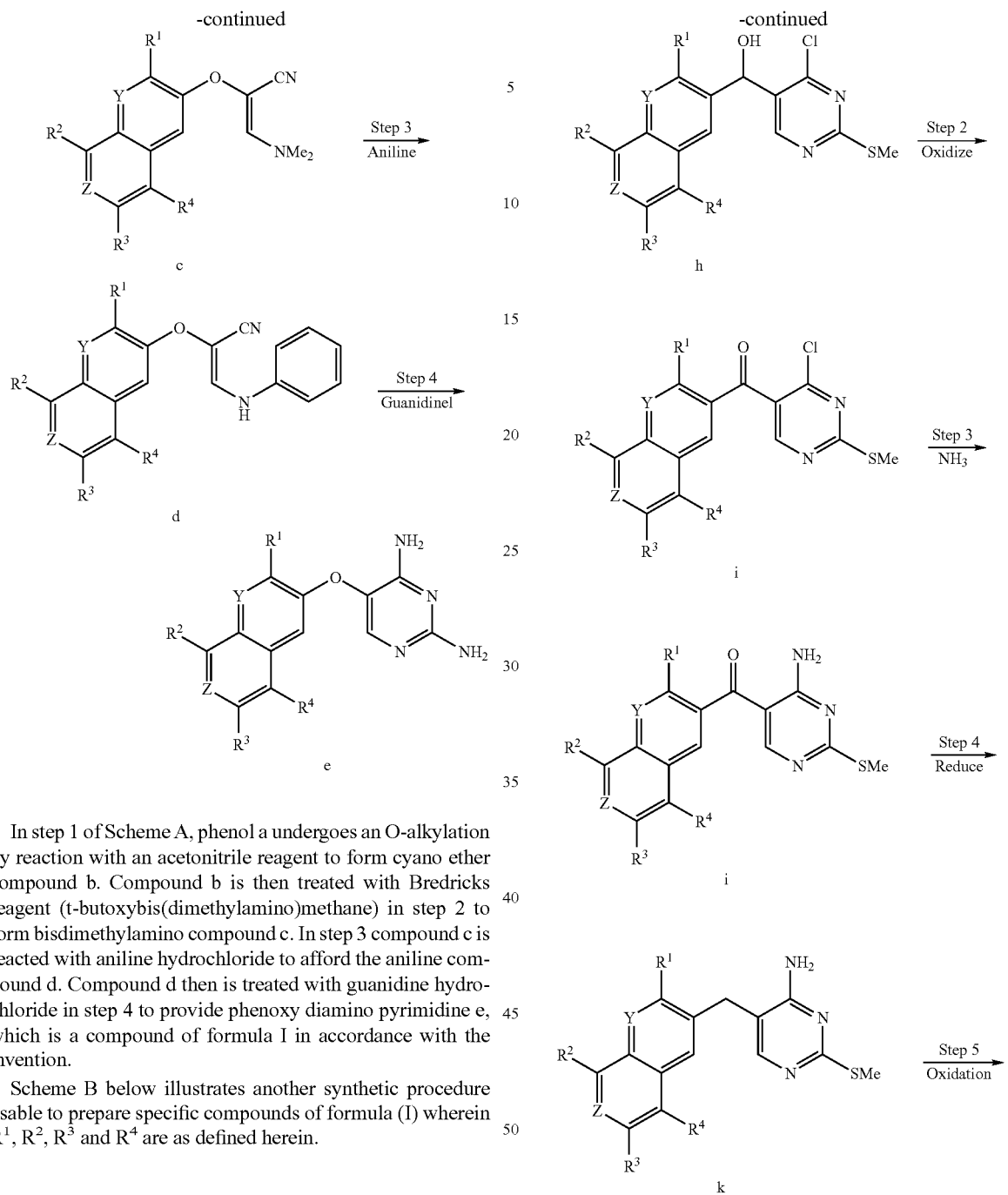

In step 1 of Scheme A, phenol a undergoes an O-alkylation by reaction with an acetonitrile reagent to form cyano ether compound b. Compound b is then treated with Bredricks reagent (t-butoxybis(dimethylamino)methane) in step 2 to form bisdimethylamino compound c. In step 3 compound c is reacted with aniline hydrochloride to afford the aniline compound d. Compound d then is treated with guanidine hydrochloride in step 4 to provide phenoxy diamino pyrimidine e, which is a compound of formula I in accordance with the invention.

Scheme B below illustrates another synthetic procedure usable to prepare specific compounds of formula (I) wherein $R^1$, $R^2$, $R^3$ and $R^4$ are as defined herein.

SCHEME B

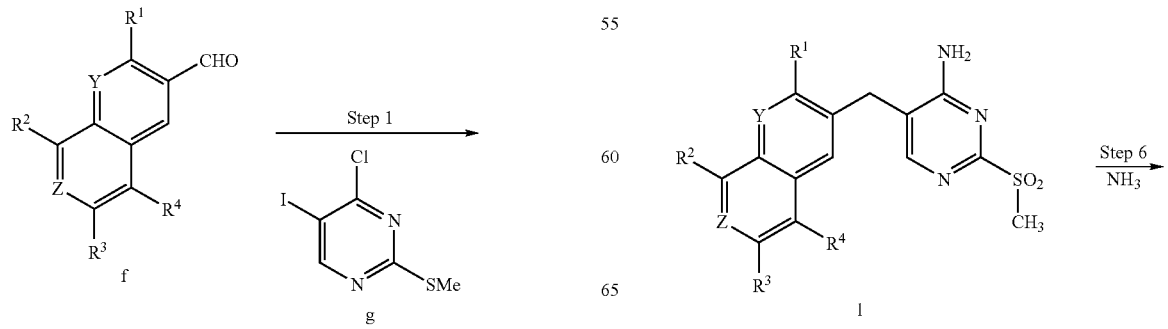

-continued

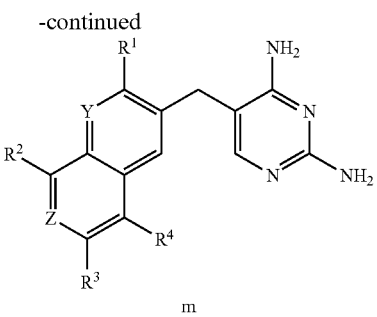

In Step 1 of Scheme B, aldehyde compound f is alkylated with the Grignard reagent derived from 4-chloro-5-iodo-2-methylsulfanyl-pyrimidine g or like iodopyrimidine to provide an hydroxy pyrimidine h. The iodopyrimidine used in this step may be prepared according to the procedure described by T. Sakamoto, et al., Chem. Pharm. Bull., 34 1986, p. 2719. In step 2, hydroxy compound h is oxidized to ketone compound i. Compound i is then subject to amination in step 3 to give aminopyridine compound j. Compound i undergoes reduction in step 4 to convert the carbonyl group to a methylene group in compound k. In step 5 sulfur oxidation is carried out to form sulfonyl compound l. In step 6 a second amination reaction is carried out to convert sulfonyl compound l to diaminopyrimidine compound m. The diamino pyrimidine m is a compound of formula I in accordance with the invention.

Specific details for producing compounds of the invention are described in the Examples section below.

Utility

The compounds of the invention are usable for the treatment of a wide range of genitorurinary diseases, conditions and disorders, including urinary tract disease states associated with bladder outlet obstruction and urinary incontinence conditions such as reduced bladder capacity, frequency of micturition, urge incontinence, stress incontinence, bladder hyperreactivity, benign prostatic hypertrophy (BPH), prostatitis, detrusor hyperreflexia, urinary frequency, nocturia, urinary urgency, overactive bladder, pelvic hypersensitivity, urethritis, prostatitits, pelvic pain syndrome, prostatodynia, cystitis, and idiophatic bladder hypersensitivity, and other symptoms related to overactive bladder.

The compounds of the invention are expected to find utility as analgesics in the treatment of diseases and conditions associated with pain from a wide variety of causes, including, but not limited to, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

Further, compounds of the invention are useful for treating respiratory disorders, including chronic obstructive pulmonary disorder (COPD), asthma, bronchospasm, and the like.

Additionally, compounds of the invention are useful for treating gastrointestinal disorders, including Irritable Bowel Syndrome (IBS), Inflammatory Bowel Disease (IBD), biliary colic and other biliary disorders, renal colic, diarrhea-dominant IBS, pain associated with GI distension, and the like.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

EXAMPLES

The following preparations and examples are given to enable those skilled in the art to more clearly understand and to practice the present invention. They should not be considered as limiting the scope of the invention, but merely as being illustrative and representative thereof.

Unless otherwise stated, all temperatures including melting points (i.e., MP) are in degrees celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The following abbreviations may be used in the Examples.

| ABBREVIATIONS | |
|---|---|
| DCM | dichloromethane/methylene chloride |
| DMF | N,N-dimethylformamide |
| DMAP | 4-dimethylaminopyridine |
| EtOAc | ethyl acetate |
| EtOH | ethanol |
| gc | gas chromatography |
| HMPA | hexamethylphosphoramide |
| hplc | high performance liquid chromatography |
| mCPBA | m-chloroperbenzoic acid |
| MeCN | acetonitrile |
| NMP | N-methyl pyrrolidinone |
| TEA | triethylamine |
| THF | tetrahydrofuran |
| LDA | lithium diisopropylamine |
| TLC | thin layer chromatography |

Preparation 1
N-(2-Hydroxyl-1-hydroxymethyl-ethyl)-guanidine

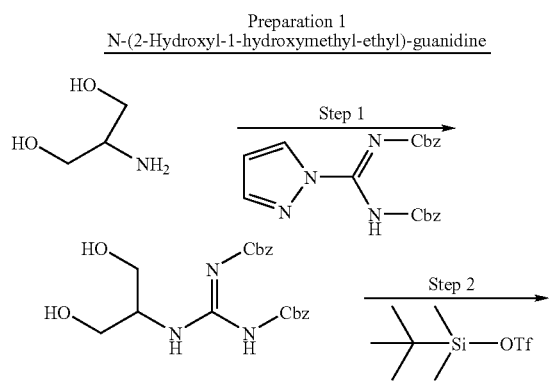

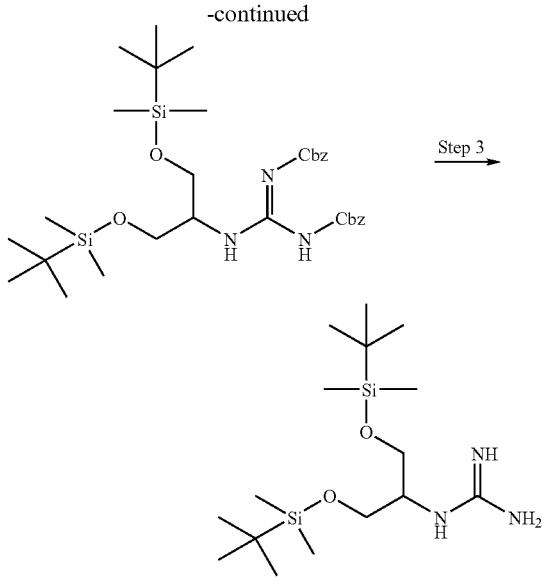

Step 1 N,N'-Bis(benzyloxycarbonyl)-N''-(2-hydroxy-1-hydroxymethyl-ethyl)-guanidine A solution of 2-amino-propane-1,3-diol (4.68 g, 50.4 mmol) and N,N'-bis(benzyloxycarbonyl)-1H-pyrrazole-1-carboxamidine (20.0 g, 52.9 mmol) in THF was stirred for 1 hour and concentrated in vacuo. The residue was washed with diethyl ether to afford N,N'-bis(benzyloxycarbonyl)-N''-(2-hydroxy-1-hydroxymethyl-ethyl)-guanidine (20.9 g, 100%) as a white solid: MS (M+H)=402.

Step 2 N,N'-Bis(benzyloxycarbonyl)-N''-[2-(tert-butyl-dimethyl-silanyloxy)-1-(tert-butyl-dimethyl-silanyloxymethyl)-ethyl]-guanidine To a 0° C. solution of N,N'-bis(benzyloxycarbonyl)-N''-(2-hydroxy-1-hydroxymethyl-ethyl)-guanidine (10.82 g, 25.6 mmol) and 2,6-lutidine (10.4 mL, 89.6 mmol) in 100 mL dichloromethane was slowly added tert-butyl-dimethylsilanyloxy triflate (18.8 mL, 81.4 mmol). After 1.5 hours the mixture was poured into cold saturated aqueous ammonium chloride, extracted with dichloromethane, dried with $Na_2SO_4$, and concentrated to give 23.42 g of an oil which solidified upon standing. The residue was washed with MeOH to afford N,N'-bis(benzyloxycarbonyl)-N''-[2-(tert-butyl-dimethyl-silanyloxy)-1-(tert-butyl-dimethyl-silanyloxymethyl)-ethyl]-guanidine (12.48 g, 74%) as a white solid: MS (M+H)=630.

Step 3 N-[2-(tert-Butyl-dimethyl-silanyloxy)-1-(tert-butyl-dimethyl-silanyloxymethyl)-ethyl]-guanidine To a solution of N,N'-bis(benzyloxycarbonyl)-N''-[2-(tert-butyl-dimethyl-silanyloxy)-1-(tert-butyl-dimethyl-silanyloxymethyl)-ethyl]-guanidine (12.48 g, 19.8 mmol) in 100 mL EtOH was added 5% Pd/C (0.5 g). The mixture was stirred under $H_2$ at 50 psi. After 2 hours the mixture was filtered through a pad of celite and concentrated in vacuo to give N-[2-(tert-butyl-dimethyl-silanyloxy)-1-(tert-butyl-dimethyl-silanyloxymethyl)-ethyl]-guanidine (7.6 g, 106%) as a white foam: MS (M+H)=362.

Example 1

5-(5-Buta-1,3-dienyl-2-iodo-4-methyl-phenoxy)-pyrimidine-2,4-diamine

The synthetic procedure used in this example is outlined below in Scheme C.

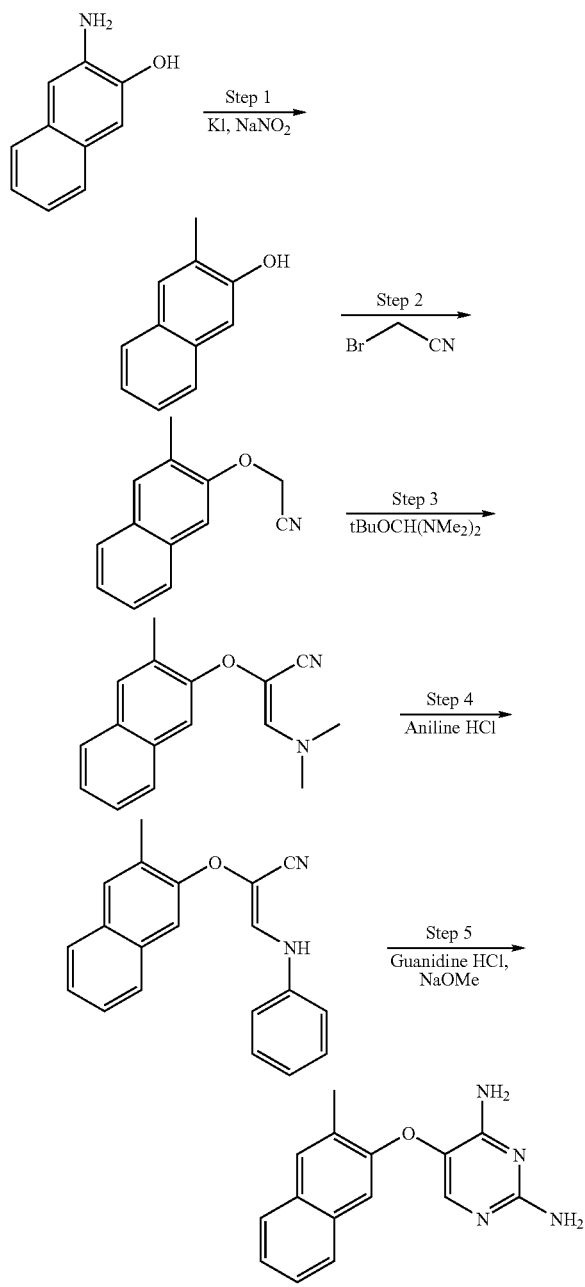

SCHEME C

Step 1 3-Iodo-naphthalen-2-ol

To a stirring solution of 3-aminonaphthol (5.41 g, 34 mmol) in 25 g of crushed ice, 30 mL of water and 10 mL of concentrated HCl at 10° C. was slowly added a solution of sodium nitrate (2.46 g, 36 mmol) in 10 mL water. A solution of potassium iodide (6.21 g, 37 mmol) in 20 mL water was slowly added with stirring at 10° C. The reaction mixture was stirred for 16 hours at room temperature, then diluted with diethyl ether and washed with water and 10% aqueous sodium sulfite solution. The organic layer was filtered through a Celite pad and the filtrate was concentrated under reduced pressure. The residue was chromatographed on silica (15% EtOAc/hexanes) to give 2.0 g of 3-iodo-naphthalen-2-ol.

Step 2 (3-Iodo-naphthalen-2-yloxy)-acetonitrile

A mixture of 3-iodo-naphthalen-2-ol (2.0 g, 7.4 mmol), bromoacetonitrile (1.066 g, 8.88 mmol) and potassium carbonate (2.04 g, 14.81 mmol) in three mL of acetonitrile was stirred at room temperature for 16 hours. The reaction mixture was diluted with methylene chloride and filtered. The filtrate was washed with 2% aqueous NaOH solution, water, and saturated brine, dried over $MgSO_4$, filtered, and concentrated under reduced pressure. The residue was crystallized from EtOAc/hexanes to give 2.07 g of (3-iodo-naphthalen-2-yloxy)-acetonitrile, MP=105-107° C., MS (M+H)=309.

Step 3 2-(5-Buta-1,3-dienyl-2-iodo-4-methyl-phenoxy)-3-dimethylamino-acrylonitrile A mixture of (3-iodo-naphthalen-2-yloxy)-acetonitrile (2.02 g, 6.53 mmol) and Bredrick's reagent ((t-butoxybis(dimethylamino)methane, 4.55 g, 26.14 mmol) was heated at 100° C. under nitrogen for 16 hours. The reaction mixture was cooled and concentrated under reduced pressure to give crude 2-(5-buta-1,3-dienyl-2-iodo-4-methyl-phenoxy)-3-dimethylamino-acrylonitrile, which was used in the same flask directly in the following step.

Step 4 2-(5-Buta-1,3-dienyl-2-iodo-4-methyl-phenoxy)-3-phenylamino-acrylonitrile To the crude crude 2-(5-buta-1,3-dienyl-2-iodo-4-methyl-phenoxy)-3-dimethylamino-acrylonitrile of step 3 was added aniline hydrochloride (2.54 g, 19.59 mmol) and ethanol (25 mL). The mixture was heated to reflux for 16 hours under nitrogen atmosphere. The mixture was cooled and concentrated under reduced pressure to yield crude 2-(5-buta-1,3-dienyl-2-iodo-4-methyl-phenoxy)-3-phenylamino-acrylonitrile, which was used in the same flask directly in the following step.

Step 5 5-(5-Buta-1,3-dienyl-2-iodo-4-methyl-phenoxy)-pyrimidine-2,4-diamine

To a suspension of guanidine hydrochloride (3.10 g, 32.5 mmol) in 10 mL ethanol was added a solution of 25% NaOMe in methanol (7.0 mL, 32.5 mmol). The resulting solution was added to the crude 2-(5-buta-1,3-dienyl-2-iodo-4-methyl-phenoxy)-3-phenylamino-acrylonitrile of step 4, and the mixture was heated to reflux under nitrogen for 16 hours. The reaction mixture was cooled, concentrated under reduced pressure, diluted with water, and extracted with methylene chloride. The organic layer was washed with water and brine, dried over magnesium sulfate, filtered and concentrated under reduced pressure. The residue was chromatographed on silica (10% MeOH/methylene chloride+0.1% $NH_4OH$), and recrystallized from EtOAc to give 2.1 g of 5-(5-buta-1,3-dienyl-2-iodo-4-methyl-phenoxy)-pyrimidine-2,4-diamine, MP=195-197° C.

Example 2

5-[2-Isopropyl-4-methyl-5-(1-methyl-buta-1,3-dienyl)-phenoxy]-pyrimidine-2,4-diamine The synthetic procedure used in this example is outlined below in Scheme D.

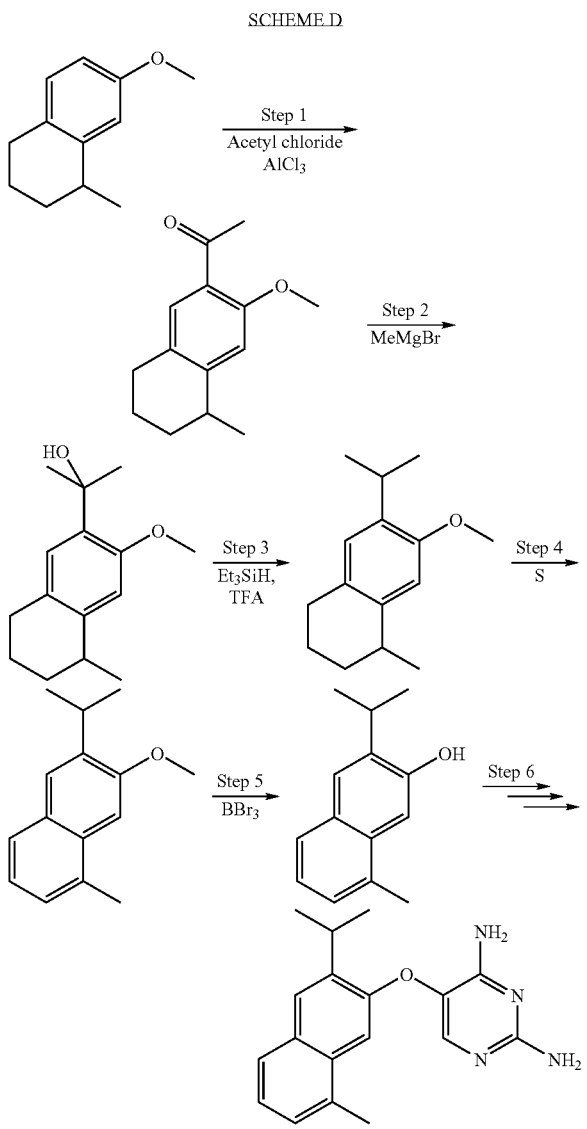

SCHEME D

Step 1 1-(3-Methoxy-5-methyl-5,6,7,8-tetrahydro-naphthalen-2-yl)-ethanone

To a stirring solution of 7-methoxy-1-methyl-1,2,3,4-tetrahydro-naphthalene (6.3 g, 35.74 mmol) in 60 mL 1,2-dichloroethane at 0° C. under nitrogen as added aluminium trichloride (5.24 g, 39.32 mmol), followed by acetyl chloride (2.8 mL, 39.32 mmol). The resulting mixture was stirred for 18 hours at room temperature, then was poured into cold 5% aqueous HCl and extracted with methylene chloride. The organic layer was separated, washed with brine, dried ($Na_2SO_4$), filtered and concentrated under reduced pressure to yield 5.1 g of 1-(3-methoxy-5-methyl-5,6,7,8-tetrahydro-naphthalen-2-yl)-ethanone, MP=48-50° C.

Step 2 2-(3-Methoxy-5-methyl-5,6,7,8-tetrahydro-naphthalen-2-yl)-propan-2-ol 1-(3-Methoxy-5-methyl-5,6,7,8-tetrahydro-naphthalen-2-yl)-ethanone (5.1 g, 23.37 mmol) was dissolved in 50 mL dry THF under nitrogen atmosphere, and the resulting solution was cooled in an ice bath. Methyl magnesium bromide (11.69 mL, 35.1 mmol in diethyl ether) was added dropwise, and the solution was stirred for one hour at 0° C., then for four hours at room temperature. The reaction mixture was poured into ice water and extracted with dichloromethane. The combined organic layers were washed with brine, dried ($Na_2SO_4$), filtered and concentrated under reduced pressure to provide 5.38 g of 2-(3-methoxy-5-methyl-5,6,7,8-tetrahydro-naphthalen-2-yl)-propan-2-ol as an oil.

Step 3

6-Isopropyl-7-methoxy-1-methyl-1,2,3,4-tetrahydro-naphthalene

To a stirred solution of 2-(3-methoxy-5-methyl-5,6,7,8-tetrahydro-naphthalen-2-yl)-propan-2-ol (5.38 g, 22.96 mmol) in methylene chloride (100 mL) at room temperature under nitrogen atmosphere, was added triethyl silane (36.6 mL, 229.6 mmol) followed by trifluoroacetic acid (17.7 mL, 229.6 mmol). The reaction mixture was stirred for five hours at room temperature, then was concentrated under reduced pressure. The residue was partitioned between methylene chloride and saturated aqueous potassium carbonate solution. The organic layer was separated, washed with brine, dried ($Na_2SO_4$), filtered and concentrated under reduced pressure. The residue was purified with flash chromatography on silica (10:0.1 hexanes/dichloromethane) to give 3.06 g of 6-isopropyl-7-methoxy-1-methyl-1,2,3,4-tetrahydro-naphthalene.

Step 4 6-Isopropyl-7-methoxy-1-methyl-naphthalene

A mixture of 6-isopropyl-7-methoxy-1-methyl-1,2,3,4-tetrahydro-naphthalene (3.06 g, 14 mmol) and sulfur (1.12 g, 35 mmol) was heated at 180° C. for one hour followed by three hours at 210-220° C. The reaction mixture was cooled and extracted with ethyl acetate. The organic layer was washed with water, dried over sodium sulfate, filtered and concentrated under reduced pressure. The residue was refluxed with copper (1.16 g, 18.2 mmol) in dry thiophene-free benzene for one hour, then cooled and filtered through Celite. The filtrate concentrated under reduced pressure and the residue was purified by flash chromatography (10:0.1 hexanes/dichloromethane) on silica to yield 2.1 g of 6-Iisopropyl-7-methoxy-1-methyl-naphthalene as an oil

Step 5 3-Isopropyl-8-methyl-naphthalen-2-ol

6-Isopropyl-7-methoxy-1-methyl-naphthalene (2.1 g, 9.79 mmol) was dissolved in 30 mL methylene chloride and the resulting solution was cooled in an ice bath. Boron tribromide (3.3 mL, 2.2 mmol in methylene chloride) was added dropwise, and the solution was stirred for one hour at 0° C. under nitrogen atmosphere, then for 18 hours at room temperature. The reaction mixture was poured into ice water and extracted with methylene chloride. The combined organic layers were washed with brine, dried ($Na_2SO_4$), filtered and concentrated under reduced pressure. The residue was purified by flash chromatography (8:1 hexanes/dichloromethane) on silica to yield 1.79 g of 3-isopropyl-8-methyl-naphthalen-2-ol as an oil.

Step 6 5-[2-Isopropyl-4-methyl-5-(1-methyl-buta-1,3-dienyl)-phenoxy]-pyrimidine-2,4-diamine Using the procedure of steps 2-5 of example 1, 3-isopropyl-8-methyl-naphthalen-2-ol was converted to 5-[2-isopropyl-4-methyl-5-(1-methyl-buta-1,3-dienyl)-phenoxy]-pyrimidine-2,4-diamine, MP=180-182° C., MS (M+H)=309.

Similarly prepared, following the procedure of Example 2 but starting with 4-methoxy-1-methyl-1,2,3,4-tetrahydronaphthalene instead of 7-methoxy-1-methyl-1,2,3,4-tetrahydro-naphthalene, was 5-(2-isopropyl-4-methyl-5-penta-1,3-dienyl-phenoxy)-pyrimidine-2,4-diamine, MP=148° C., MS (M+H)=309.

Example 3

5-(3-Isopropyl-6-methoxy-naphthalen-2-yloxy)-pyrimidine-2,4-diamine

The synthetic procedure used in this example is outlined below in Scheme E.

SCHEME E

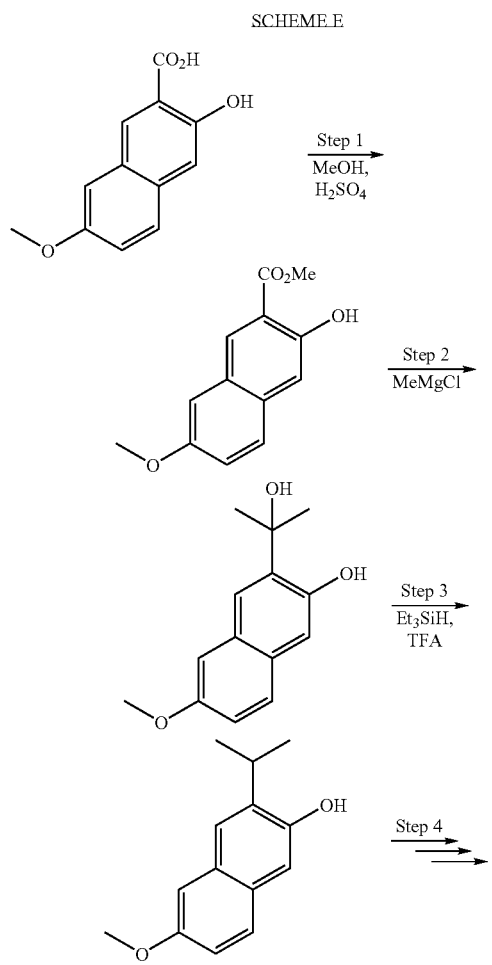

-continued

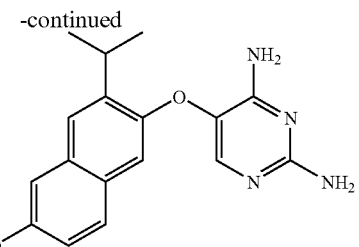

Step 1
3-Hydroxy-7-methoxy-naphthalene-2-carboxylic acid methyl ester

To a solution of 3-hydroxy-7-methoxy-naphthalene-2-carboxylic acid (2.5 g, 11.45 mmol) in 50 mL methanol was added 0.3 mL of concentrated sulfuric acid. The resulting mixture was heated at reflux for 18 hours, then cooled and diluted with diethyl ether. The organic phase was washed with water and saturated aqueous sodium bicarbonate, dried ($Na_2SO_4$), filtered and concentrated under reduced pressure to give 2.51 g of 3-hydroxy-7-methoxy-naphthalene-2-carboxylic acid methyl ester, MP=129-131° C.

Step 2 3-(1-Hydroxy-1-methyl-ethyl)-6-methoxy-naphthalen-2-ol

3-Hydroxy-7-methoxy-naphthalene-2-carboxylic acid methyl ester (2.51 g, 10.8 mmol) was dissolved in 50 mL dry THF, and the resulting solution was cooled in an ice bath under nitrogen atmosphere. Methyl magnesium chloride (10.8 mL, 32.4 mmol in THF) was added dropwise, and the reaction mixture was stirred for six hours at 0° C. under nitrogen atmosphere. The reaction mixture was poured into ice water and extracted with dichloromethane. The combined organic layers were washed with saturated aqueous $NH_4Cl$, dried ($Na_2SO_4$), filtered and concentrated under reduced pressure to yield 2.4 g of 3-(1-hydroxy-1-methyl-ethyl)-6-methoxy-naphthalen-2-ol as a pale yellow solid, MP=148-150° C.

Step 3 3-Isopropyl-6-methoxy-naphthalen-2-ol

To a stirring solution of 3-(1-hydroxy-1-methyl-ethyl)-6-methoxy-naphthalen-2-ol (2.4 g, 10.33 mmol) in 50 mL dichloromethane at room temperature under nitrogen atmosphere, was added triethyl silane (16.5 mL, 103.3 mmol) followed by trifluoroacetic acid (7.96 mL, 103.3 mmol). The reaction mixture was stirred for 40 minutes, after which solvent was removed under reduced pressure. The residue was partitioned between dichloromethane and saturated aqueous potassium carbonate solution. The organic layer was washed with water and brine, dried ($Na_2SO_4$), filtered and concentrated under reduced pressure to give 1.2 g of 3-isopropyl-6-methoxy-naphthalen-2-ol as an oil.

Step 4 5-(3-Isopropyl-6-methoxy-naphthalen-2-yloxy)-pyrimidine-2,4-diamine

Using the procedure of steps 2-5 of example 1, 3-isopropyl-6-methoxy-naphthalen-2-ol was converted to 5-(3-isopropyl-6-methoxy-naphthalen-2-yloxy)-pyrimidine-2,4-diamine, MP=170-172° C., MS (M+H)=325.

Example 4

5-(2-Isopropyl-quinolin-3-yloxy)-pyrimidine-2,4-diamine

The synthetic procedure used in this example is outlined below in Scheme F.

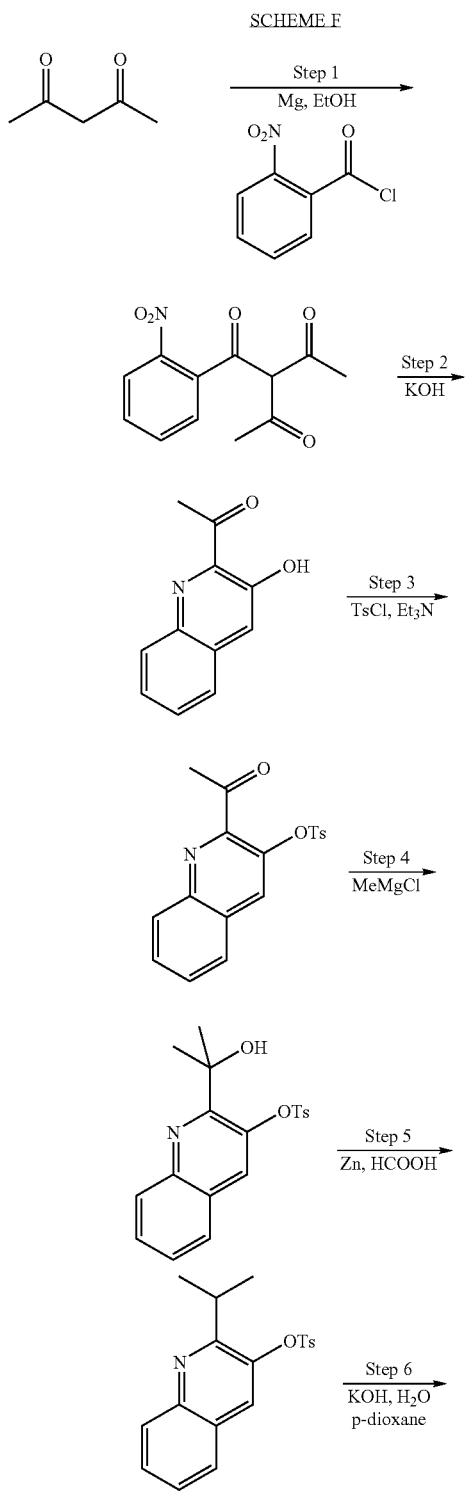

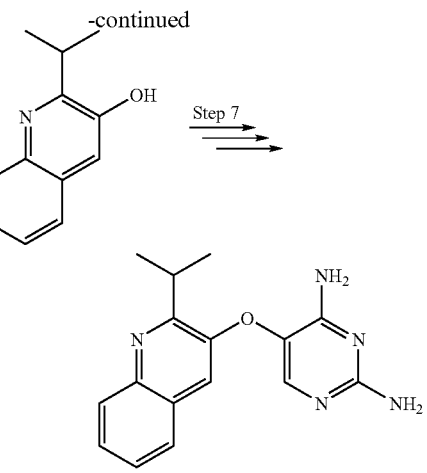

Step 1 3-(2-Nitro-benzoyl)-pentane-2,4-dione

Magnesium ethoxide was generated by refluxing ethanol (50 mL) with 1.2 g (50 mmol) Magnesium turnings for 3 days. The ethanol was removed under reduced pressure, and 50 mL of toluene was added, followed by dropwise addition of 5 g (50 mmol) of 2,5-pentanedione. The reaction mixture was stirred at room temperature for two hours and then at 70° C. for one hour, and then cooled to −10° C. A solution of 9.27 g (50 mmol) of 2-nitrobenzoyl chloride in 20 mL of toluene was added dropwise, and the solution was stirred at ambient temperature for 18 hours. The reaction mixture was poured into a mixture of ice and 1N HCl, and the resulting solution was extracted with ethyl acetate. The organic layert was washed with brine, dried (MgSO$_4$) filtered and concentrated to dryness under reduced pressure to afford 12.23 g of 3-(2-nitro-benzoyl)-pentane-2,4-dione Step 2 1-(3-Hydroxy-quinolin-2-yl)-ethanone 3-(2-Nitro-benzoyl)-pentane-2,4-dione (12.23 g, 49.7 mmol) was heated with 150 mL of 20% (w/v) aqueous KOH to 120° C. for 30 minutes. The mixture was cooled to 5° C. and neutralized with 6N HCl. The resulting precipitate was filtered and washed with water (500 mL), air dried, and purified by column chromatography with silica eluting with 20% ethyl acetate in hexane to afford 5.4 g of 1-(3-Hydroxy-quinolin-2-yl)-ethanone as a yellow solid.

Step 3

Toluene-4-sulfonic acid 2-acetyl-quinolin-3-yl ester

To a cooled (5° C.) solution of 1-(3-Hydroxy-quinolin-2-yl)-ethanone (1.96 g, 10.5 mmol) in 100 mL dichloromethane was added triethylamine (1.59 g, 2.19 mL. 15.75 mmol). After 10 minutes p-toluenesulfonyl chloride (2.191 g, 11.5 mmol) was added and the mixture was stirred at room temperature for 18 hours. The mixture was washed with 1N HCl, water, and brine, dried (MgSO$_4$) and concentrated under reduced pressure to afford 3.58 g of toluene-4-sulfonic acid 2-acetyl-quinolin-3-yl ester.

Step 4 Toluene-4-sulfonic acid 2-(1-hydroxy-1-methyl-ethyl)-quinolin-3-yl ester Toluene-4-sulfonic acid 2-acetyl-quinolin-3-yl ester (3.58 g, 10.5 mmol) in 40 mL of THF was cooled to around −20 to −25° C. Methyl magnesium chloride (5.25 mL of 3M solution in THF) was added dropwise over a period of 10 minutes. The reaction mixture was allowed to stir 18 hours at ambient temperature, and then was poured into saturated aqueous $NH_4Cl$ and acidified with 1N HCl to pH 5. The resulting mixture was extracted with ethyl acetate and the combined organic phases were washed with brine, dried ($MgSO_4$), filtered and concentrated to dryness under reduced pressure to give 3.75 g of toluene-4-sulfonic acid 2-(1-hydroxy-1-methyl-ethyl)-quinolin-3-yl ester as an oil that solidified on standing.

Step 5 Toluene-4-sulfonic acid 2-isopropyl-quinolin-3-yl ester

Toluene-4-sulfonic acid 2-(1-hydroxy-1-methyl-ethyl)-quinolin-3-yl ester (3.75 g, 10.5 mmol) was stirred in 50 mL of formic acid for 10 minutes, and zinc dust (3.43 g, 5.25 mmol) was added. The reaction mixture was stirred for four hours and then was added cautiously to a mixture of 100 mL aqueous saturated $NaHCO_3$ and 100 g of ice. The resulting aqueous mixture was neutralized to pH7 by addition of aqueous saturated $NaHCO_3$, and was extracted with ethyl acetate. The combined organic layers were washed with brine, dried ($MgSO_4$) and concentrated under reduced pressure. The residue was purified by column chromatography using silica eluting with 10% ethyl acetate in hexanes to afford 1.35 g of toluene-4-sulfonic acid 2-isopropyl-quinolin-3-yl ester.

Step 6 2-Isopropyl-quinolin-3-ol

A mixture of toluene-4-sulfonic acid 2-isopropyl-quinolin-3-yl ester (1.31 g, 3.8 mmol), 0.64 g (11.4 mmol) of KOH in 10 mL of water, and 50 mL of p-dioxane was heated to refluxe for 1.5 hours until completion. The p-dioxane was removed under reduced pressure and the residue was diluted with water and acidified with 1N HCl to pH=6. The aqueous solution was extracted with ethyl acetate and the combined organic layers were washed with brine, dried ($MgSO_4$) and concentrated under reduced pressure to afford quantitatively 0.71 g of 2-isopropyl-quinolin-3-ol

Step 7 5-(2-Isopropyl-quinolin-3-yloxy)-pyrimidine-2,4-diamine

2-Isopropyl-quinolin-3-ol was converted to 5-(2-isopropyl-quinolin-3-yloxy)-pyrimidine-2,4-diamine following the procedure of steps 2-5 of Example 1: MP=285.0-285.6° C.

Similarly prepared were 5-(2-Isopropyl-6-methyl-quinolin-3-yloxy)-pyrimidine-2,4-diamine (MP=239.4-242.1° C.) and 5-(2-Isopropyl-8-methyl-quinolin-3-yloxy)-pyrimidine-2,4-diamine (MP=248.3-249.4° C.).

Example 5

5-(7-Isopropyl-quinolin-6-yloxy)-pyrimidine-2,4-diamine

The synthetic procedure used in this example is outlined below in Scheme G.

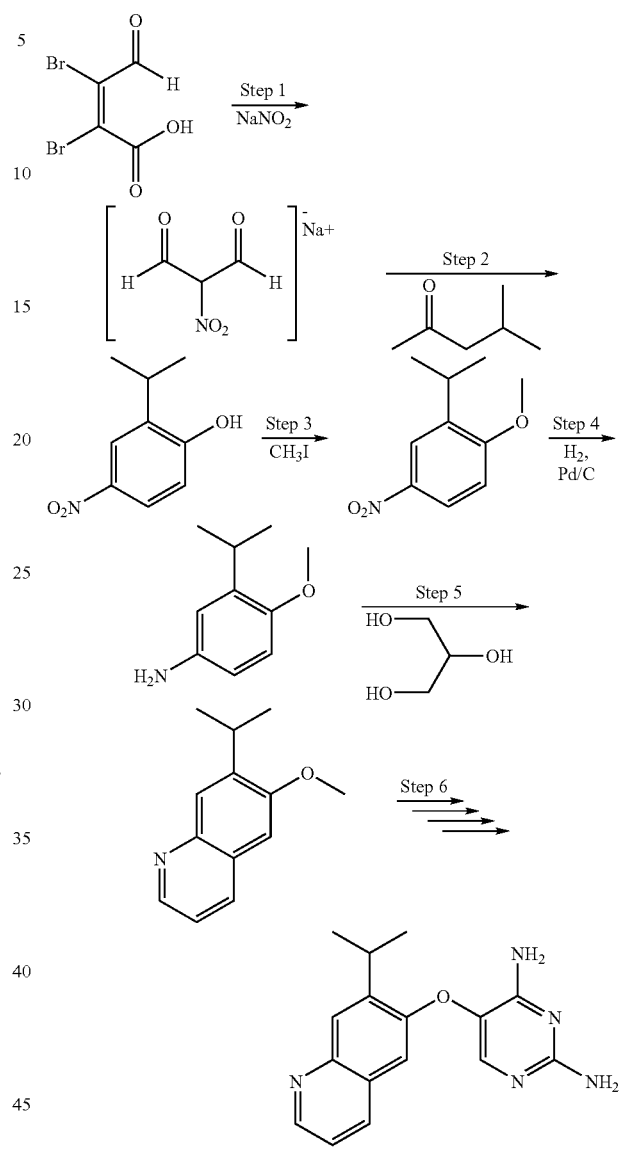

SCHEME G

Step 1 Sodium Nitromalonaldehyde

Sodium nitromalonaldehyde monohydrate was prepared in this step from mucobromic acid as described in Org. Syn. Collective Volume 4 (1963), page 844. Sodium nitrite (51.6 g, 748 mmol) in 50 mL of water was heated to 54° C., and 51.6 g (200 mmol) of mucobromic acid in 50 mL of ethanol was added dropwise over a period of two hours, during which time the temperature of the mixture was kept at 54° C. Stirring was continued for 10 minutes at 54° C. after addition, then heat was removed and the mixture was cooled in an ice bath. The resulting precipitate was filtered and the solid was washed with 150 mL of ethanol-water mixture (1:1). The solid was heated with 80 mL of ethanol and 20 mL of water to reflux for one hour, then filtered while hot and the filtrate was cooled (5° C.). A precipitate formed during cooling and was filtered and air dried, affording 9.17 g of sodium nitromalonaldehyde monohydrate.

Step 2 2-Isopropyl-4-nitrophenol

4-Methyl-2-pentanone (4.85 g, 48 mmol) in 40 mL of ethanol was added dropwise to a solution of sodium nitromalonaldehyde monohydrate (7.61 g, 48 mmol) in 40 mL of water. NaOH (48 ml of 1N aqueous solution) was then added to the reaction mixture. The mixture was stirred at room temperature overnight, and solvent was removed under reduced pressure. The residue was diluted with water and neutralized, then extracted with ethyl acetate. The combined organic layers were washed with brine, dried (MgSO$_4$), filtered and concentrated under reduced pressure. The resulting residue was purified by column chromatography with silica eluting with 15% ethyl acetate in hexanes to yield 4.7 g of 2-isopropyl-4-nitrophenol.

Step 3 2-Isopropyl-1-methoxy-4-nitro-benzene

2-Isopropyl-4-nitrophenol (4.7 g, 26 mmol) was dissolved in 100 mL of acetone, and 5.4 g (39 mmol) of K$_2$CO$_3$ was added, followed by 14.8 g (6.5 mL, 104 mmol) of iodomethane. The reaction flask was capped and the mixture was stirred at room temperature for 17 hours. The mixture was concentrated under reduced pressure, diluted with water and extracted with ethyl acetate. The combined organic layers were washed with brine, dried (MgSO$_4$), filtered and concentrated under reduced pressure to afford 4.53 g of 3-isopropyl-4-methoxynitrobenzene.

Step 4 3-Isopropyl-4-methoxy-phenylamine

2-Isopropyl-1-methoxy-4-nitro-benzene (4.53 g, 23.6 mmol) was dissolved in 100 mL of methanol in presence of 0.4 g of 10% Pd/C in a Parr bottle, and then subjected to 40 psi of H$_2$ overnight at room temperature. The mixture was purged with nitrogen for 10 minutes and filtered over Celite. The filtrate was concentrated to give 4.22 g 3-isopropyl-4-methoxyaniline.

Step 5 7-Isopropyl-6-methoxy-quinoline

A mixture of 3-isopropyl-4-methoxyaniline (4.22 g, 23.6 mmol), 5.87 g (63.7 mmole) of glycerol and 3.25 g (14 mmol) of As$_2$O$_5$ was heated to 100° C. with stirring At 100° C., 4.0 mL of concentrated H$_2$SO$_4$ was added dropwise. The mixture was heated at 150-160° C. for six hours, then cooled to 80° C., and 20 mL water was added, followed by aqueous saturated NaHCO$_3$ until the mixture reached pH7-8. The mixture was diluted with 100 mL of water and 300 mL of ethyl acetate and the solution mixture was decanted from insolubles. The organic layer was separated, washed with brine, dried (MgSO$_4$), filtered and concentrated under reduced pressure. The resulting residue was purified by column chromatography with silica eluting with 20% ethyl acetate in hexanes to give 2.58 g of 7-isopropyl-6-methoxyquinoline, together with 0.65 g of 6-hydroxy-7-isopropylquinoline as a minority product.

Step 6 5-(7-Isopropyl-quinolin-6-yloxy)-pyrimidine-2,4-diamine

7-Isopropyl-6-methoxyquinoline was converted to 5-(7-isopropyl-quinolin-6-yloxy)-pyrimidine-2,4-diamine using the procedure of steps 2-5 of Example 1: MP=206.9-208.2° C., MS (M+H)=296.

Example 6

2-[4-Amino-5-(7-isopropyl-quinolin-6-yloxy)-pyrimidin-2-ylamino]-propane-1,3-diol The synthetic procedure used in this example is outlined below in Scheme H.

SCHEME H

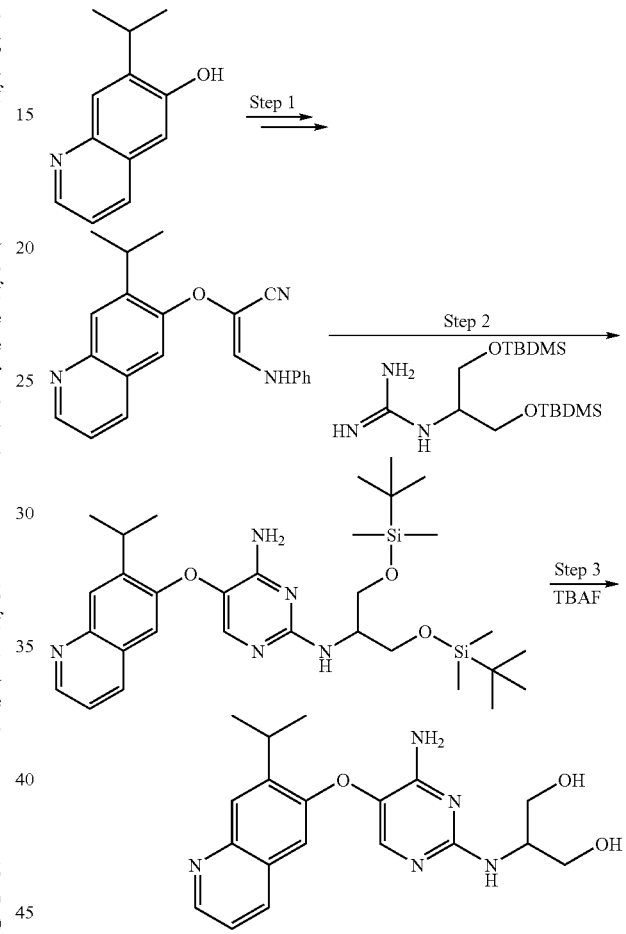

Step 1 N2-[2-(tert-Butyl-dimethyl-silanyloxy)-1-(tert-butyl-dimethyl-silanyloxymethyl)-ethyl]-5-(7-isopropyl-quinolin-6-yloxy)-pyrimidine-2,4-diamine 7-Isopropyl-6-methoxy-quinoline (Example 5) was converted to 7-isopropyl-quinolin-6-ol following the procedure of step 5 of Example 2. 7-Isopropyl-quinolin-6-ol was in turn converted to 2-(7-isopropyl-quinolin-6-yloxy)-3-phenylamino-acrylonitrile following the procedure of steps 2-4 of Example 1.

Step 2 N2-[2-(tert-Butyl-dimethyl-silanyloxy)-1-(tert-butyl-dimethyl-silanyloxymethyl)-ethyl]-5-(7-isopropyl-quinolin-6-yloxy)-pyrimidine-2,4-diamine A mixture of 2-(7-isopropyl-quinolin-6-yloxy)-3-phenylamino-acrylonitrile (100 mg, 0.3 mmol) and N-[2-(tert-butyl-dimethyl-silanyloxy)-1-(tert-butyl-dimethyl-silanyloxymethyl)-ethyl]-guanidine (220 mg, 0.6 mmol) in 3 mL EtOH was heated with a microwave at 165° C. for 15 min. The resultant solution was concentrated and the residue was partitioned between water and dichloromethane and the aqueous layer was extracted with dichloromethane. The combined organic layers were dried with $Na_2SO_4$, and concentrated to give 270 mg of a brown oil. Purification via flash chromatography (ethyl acetate/hexanes) gave N2-[2-(tert-butyl-dimethyl-silanyloxy)-1-(tert-butyl-dimethyl-silanyloxymethyl)-ethyl]-5-(7-isopropyl-quinolin-6-yloxy)-pyrimidine-2,4-diamine (120 mg, 67%): MS (M+H)=598.

Step 3 2-[4-Amino-5-(7-isopropyl-quinolin-6-yloxy)-pyrimidin-2-ylamino]-propane-1,3-diol A solution of N2-[2-(tert-butyl-dimethyl-silanyloxy)-1-(tert-butyl-dimethyl-silanyloxymethyl)-ethyl]-5-(7-isopropyl-quinolin-6-yloxy)-pyrimidine-2,4-diamine (120 mg, 0.2 mmol) and tetrabutylammonium fluoride (1M in THF, 0.6 mL, 0.6 mmol) in 5 mL THF was stirred for 2 h and partitioned between water and EtOAc. The aqueous layer was extracted with EtOAc, washed with brine, dried with $Na_2SO_4$, and concentrated to give 110 mg of a tan oil. Purification via preparative thin layer chromatography (113:19:1 $CH_2Cl_2$: MeOH:concentrated ammonium hydroxide) followed by crystallization using cold diethyl ether, ethyl acetate, methylene chloride, and methanol afforded 2-[4-amino-5-(7-isopropyl-quinolin-6-yloxy)-pyrimidin-2-ylamino]-propane-1,3-diol (50 mg, 67%): MP=171.9-174.4° C., MS (M+H)=370.

Example 7

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | Grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 8

$P2X_3/P2X_{2/3}$ FLIPR (Fluorometric Imaging Plate Reader) Assay

CHO-K1 cells were transfected with cloned rat $P2X_3$ or human $P2X_{2/3}$ receptor subunits and passaged in flasks. 18-24 hours before the FLIPR experiment, cells were released from their flasks, centrifuged, and resuspended in nutrient medium at $2.5 \times 10^5$ cells/ml. The cells were aliquoted into black-walled 96-well plates at a density of 50,000 cells/well and incubated overnight in 5% $CO_2$ at 37° C. On the day of the experiment, cells were washed in FLIPR buffer (calcium- and magnesium-free Hank's balanced salt solution, 10 mM HEPES, 2 mM $CaCl_2$, 2.5 mM probenecid; FB). Each well received 100 µl FB and 100 µl of the fluorescent dye Fluo-3 AM [2 µM final conc.]. After a 1 hour dye loading incubation at 37° C., the cells were washed 4 times with FB, and a final 75 µl/well FB was left in each well.

Test compounds (dissolved in DMSO at 10 mM and serially diluted with FB) or vehicle were added to each well (25 µl of a 4X solution) and allowed to equilibrate for 20 minutes at room temperature. The plates were then placed in the FLIPR and a baseline fluorescence measurement (excitation at 488 nm and emission at 510-570 nm) was obtained for 10 seconds before a 100 l/well agonist or vehicle addition. The agonist was a 2X solution of α,β-meATP producing a final concentration of 1 µM ($P2X_3$) or 5 µM ($P2X_{2/3}$). Fluorescence was measured for an additional 2 minutes at 1 second intervals after agonist addition. A final addition of ionomycin (5 µM, final concentration) was made to each well of the FLIPR test plate to establish cell viability and maximum fluorescence of dye-bound cytosolic calcium. Peak fluorescence in response to the addition of α,β-meATP (in the absence and presence of test compounds) was measured and inhibition curves generated using nonlinear regression. PPADS, a standard P2X antagonist, was used as a positive control.

Using the above procedure, compounds of the invention exhibited activity for the $P2X_3$ receptor. The compound 5-(7-Isopropyl-quinolin-6-yloxy)-pyrimidine-2,4-diamine, for example, exhibited a $pIC_{50}$ of approximately 7.42 for the $P2X_3$ receptor, and approximately 7.30 for the $P2X_{2/3}$ receptor, using the above assay.

Example 9

In Vivo Assay for Asthma and Lung Function

BALb/cJ mice are immunized with a standard immunization protocol. Briefly, mice (N=8/group) are immunized i.p. with ovalbumin (OVA; 10 µg) in alum on days 0 and 14. Mice are then challenged with aerosolized OVA (5%) on day 21 and 22. Animals receive vehicle (p.o.) or a compound of the invention (100 mg/kg p.o.) all starting on day 20.

Lung function is evaluated on day 23 using the Buxco system to measure PenH in response to an aerosol methacholine challenge. Mice are then euthanized and plasma samples collected at the end of the study.

Example 10

Volume Induced Bladder Contraction Assay

Female Sprague-Dawley rats (200-300 g) were anesthetized with urethane (1.5 g/kg, sc). The animals were tracheotomized, and a carotid artery and femoral vein were cannulated for blood pressure measurement and drug administration, respectively. A laparotomy was performed and the ureters were ligated and transected proximal to the ligation. The external urethral meatus was ligated with silk suture and the urinary bladder was cannulated via the dome for saline infusion and bladder pressure measurement.

Following a 15-30 minute stabilization period the bladder was infused with room temperature saline at 100 µl/min until continuous volume-induced bladder contractions (VIBCs) were observed. The infusion rate was then lowered to 3-5 µl/min for 30 minutes before the bladder was drained and allowed to rest for 30 minutes. All subsequent infusions were performed as indicated except the lower infusion rate was maintained for only 15 minutes instead of 30 minutes. Bladder filling and draining cycles were repeated until the threshold volumes (TV; the volume needed to trigger the first micturition bladder contraction) varied by less than 10% for two consecutive baselines and contraction frequency was within 2 contractions for a 10 minute period following the slower infusion rate. Once reproducible TVs and VIBCs were established the bladder was drained and the animal was dosed with drug or vehicle (0.5 ml/kg, i.v.) 3 minutes prior to the start of the next scheduled infusion.

Example 11

Formalin Pain Assay

Male Sprague Dawley rats (180-220 g) are placed in individual Plexiglas cylinders and allowed to acclimate to the testing environment for 30 min. Vehicle, drug or positive control (morphine 2 mg/kg) is administered subcutaneously at 5 ml/kg. 15 min post dosing, formalin (5% in 50 µl) is injected into plantar surface of the right hind paw using a 26-gauge needle. Rats are immediately put back to the observation chamber. Mirrors placed around the chamber allow unhindered observation of the formalin-injected paw. The duration of nociphensive behavior of each animal is recorded by a blinded observer using an automated behavioral timer. Hindpaw licking and shaking/lifting are recorded separately in 5 min bin, for a total of 60 min. The sum of time spent licking or shaking in seconds from time 0 to 5 min is considered the early phase, whereas the late phase is taken as the sum of seconds spent licking or shaking from 15 to 40 min. A plasma sample is collected.

Example 12

Colon Pain Assay

Adult male Sprague-Dawley rats (350-425 g; Harlan, Indianapolis, Ind.) are housed 1-2 per cage in an animal care facility. Rats are deeply anesthetized with pentobarbital sodium (45 mg/kg) administered intraperitoneally. Electrodes are placed and secured into the external oblique musculature for electromyographic (EMG) recording. Electrode leads are tunneled subcutaneously and exteriorized at the nape of the neck for future access. After surgery, rats are housed separately and allowed to recuperate for 4-5 days prior to testing.

The descending colon and rectum are distended by pressure-controlled inflation of a 7-8 cm-long flexible latex balloon tied around a flexible tube. The balloon is lubricated, inserted into the colon via the anus, and anchored by taping the balloon catheter to the base of the tail. Colorectal distension (CRD) is achieved by opening a solenoid gate to a constant pressure air reservoir. Intracolonic pressure is controlled and continuously monitored by a pressure control device. Response is quantified as the visceromotor response (VMR), a contraction of the abdominal and hindlimb musculature. EMG activity produced by contraction of the external oblique musculature is quantified using Spike2 software (Cambridge Electronic Design). Each distension trial lasts 60 sec, and EMG activity is quantified for 20 sec before distension (baseline), during 20 sec distension, and 20 sec after distention. The increase in total number of recorded counts during distension above baseline is defined as the response. Stable baseline responses to CRD (10, 20, 40 and 80 mmHg, 20 seconds, 4 minutes apart) are obtained in conscious, unsedated rats before any treatment.

Compounds are evaluated for effects on responses to colon distension initially in a model of acute visceral nociception and a model of colon hypersensitivity produced by intracolonic treatment with zymosan (1 mL, 25 mg/mL) instilled into the colon with a gavage needle inserted to a depth of about 6 cm. Experimental groups will consist of 8 rats each.

Acute visceral nociception: For testing effects of drug on acute visceral nociception, 1 of 3 doses of drug, vehicle or positive control (morphine, 2.5 mg/kg) are administered after baseline responses are established; responses to distension are followed over the next 60-90 minutes.

Visceral hypersensitivity: For testing effects of drug or vehicle after intracolonic treatment with zymosan, intracolonic treatment is given after baseline responses are established. Prior to drug testing at 4 hours, responses to distension are assessed to establish the presence of hypersensitivity. In zymosan-treated rats, administration of 1 of 3 doses of drug, vehicle or positive control (morphine, 2.5 mg/kg) are given 4 hours after zymosan treatment and responses to distension followed over the next 60-90 minutes.

Example 13

Cold Allodynia in Rats with a Chronic Constriction Injury of the Sciatic Nerve

The effects of compounds of this invention on cold allodynia are determined using the chronic constriction injury (CCI) model of neuropathic pain in rats, where cold allodynia is measured in a cold-water bath with a metal-plate floor and water at a depth of 1.5-2.0 cm and a temperature of 3-4° C. (Gogas, K. R. et al., Analgesia, 1997, 3, 1-8).

Specifically, CCI, rats are anesthetized; the trifurcation of the sciatic nerve is located and 4 ligatures (4-0, or 5-0 chromic gut) are placed circumferentially around the sciatic nerve proximal to the trifurcation. The rats are then allowed to recover from the surgery. On days 4-7 after surgery, the rats are initially assessed for cold-induced allodynia by individually placing the animals in the cold-water bath and recording the total lifts of the injured paw during a 1-min period of time: The injured paw is lifted out of the water. Paw lifts associated with locomotion or body repositioning are not recorded. Rats that displayed 5 lifts per min or more on day 4-7 following surgery are considered to exhibit cold allodynia and are used in subsequent studies. In the acute studies, vehicle, reference compound or compounds of this invention are administered subcutaneously (s.c.) 30 min before testing. The effects of repeated administration of the compounds of this invention on cold allodynia are determined 14, 20 or 38 h following the last oral dose of the following regimen: oral (p.o.) administration of vehicle, reference or a compound of this invention at ~12 h intervals (BID) for 7 days.

Example 14

Cancer Bone Pain in C3H/HeJ Mice

The effects of compounds of this invention on bone pain are determined between Day 7 to Day 18 following intramedullary injection of 2472 sarcoma cells into the distal femur of C3H/HeJ mice.

Specifically, NCTC 2472 tumor cells (American Type Culture Collection, ATCC), previously shown to form lytic lesions in bone after intramedullary injection, are grown and maintained according to ATCC recommendations. Approximately $10^5$ cells are injected directly into the medullary cavity of the distal femur in anesthetized C3H/HeJ mice. Beginning on about Day 7, the mice are assessed for spontaneous nocifensive behaviors (flinching & guarding), palpation-evoked nocifensive behaviors (flinching & guarding), forced ambulatory guarding and limb use. The effects of compounds of this invention are determined following a single acute (s.c.) administration on Day 7-Day 15. In addition, the effects of repeated (BID) administration of compounds of this invention from Day 7-Day 15 are determined within 1 hour of the first dose on Days 7, 9, 11, 13 and 15.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of formula I:

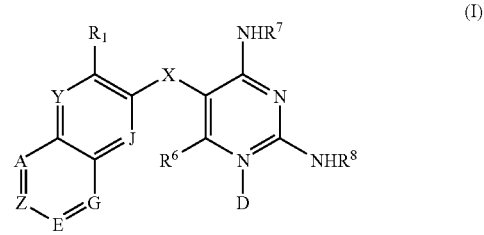

or a pharmaceutically acceptable salt thereof, wherein:

X is:

—O—;

D is an optional oxygen;

A is N and E, G, J, Y and Z are $CR^a$;

$R^1$ is:
  alkyl;
  alkenyl;
  alkynyl;
  cycloalkyl;
  cycloalkenyl;
  halo;
  haloalkyl; or
  hydroxyalkyl;
each $R^a$ is independently:
  hydrogen;
  alkyl;
  alkenyl;
  amino;
  aminosulfonyl;
  halo;
  amido;
  haloalkyl;
  alkoxy;
  hydroxy;
  haloalkoxy;
  nitro;
  hydroxyalkyl;
  alkoxyalkyl;
  hydroxyalkoxy;
  alkynylalkoxy;
  alkylsulfonyl;
  arylsulfonyl;
  cyano;
  aryl;
  heteroaryl;
  heterocyclyl;
  heterocyclylalkoxy;
  aryloxy;
  heteroaryloxy;
  aralkyloxy;
  heteroaralkyloxy;
  optionally substituted phenoxy;
  —C≡C—$R^b$—;
  —(CH$_2$)$_m$—(Z)$_n$—(CO)—$R^c$;
  —(CH$_2$)$_m$—(Z)$_n$—SO$_2$—(NR$^d$)$_n$—$R^c$;
  wherein
    m and n each independently is 0 or 1,
    Z is O or NR$^d$,
    $R^b$ is hydrogen; alkyl; aryl; aralkyl; heteroaryl; heteroaralkyl; hydroxyalkyl; alkoxyalkyl; alkylsulfonylalkyl; aminoalkyl; cyanoalkyl; alkylsilyl; cycloalkyl, cycloalkylalkyl; heterocyclyl; and heterocyclylalkyl;
    $R^c$ is hydrogen, alkyl, hydroxy, alkoxy, amino, hydroxyalkyl or alkoxyalkyl, and
    each $R^d$ is independently hydrogen or alkyl;
$R^6$ is:
  hydrogen;
  alkyl;
  halo;
  haloalkyl;
  amino; or
  alkoxy;
$R^7$ and $R^8$ each independently is:
  hydrogen;
  alkyl;
  cycloalkyl;
  cycloalkylalkyl;
  haloalkyl;
  haloalkoxy;
  hydroxyalkyl;
  alkoxyalkyl;
  alkylsulfonyl;
  alkylsulfonylalkyl;
  aminocarbonyloxyalkyl;
  hydroxycarbonylalkyl;
  hydroxyalkyloxycarbonylalkyl;
  aryl;
  aralkyl;
  arylsulfonyl;
  heteroaryl;
  heteroarylalkyl;
  heteroarylsulfonyl;
  heterocyclyl;
  heterocyclylalkyl; or
  —(C═O)—$R^e$;
  wherein
    $R^e$ is alkyl, alkoxy, cycloalkyl, cycloalkoxy, cycloalkylalkyl, cycloalkylalkoxy, aryl, aryloxy, heteroaryl, heteroaryloxy, aralkyl, aralkoxy, heteroaralkyl, heteroaralkoxy, —(CH$_2$)$_p$—C(═O)—$R^f$, —(CH═CH)—C(═O)—$R^f$, or —CH(NH$_2$)—$R^g$
    wherein
      $R^f$ is hydrogen, hydroxy, alkyl, alkoxy, cycloalkyl, cycloalkoxy, cycloalkylalkyl, cycloalkylalkoxy, aryl, aryloxy, heteroaryl, heteroaryloxy, aralkyl, aralkoxy, heteroaralkyl, heteroaralkoxy, or amino;
      p is 2 or 3;
      $R^g$ is hydrogen, alkyl, hydroxyalkyl, aminoalkyl, optionally substituted phenyl, benzyl, guanidinylalkyl, carboxyalkyl, amidoalkyl, thioalkyl or imidazolalkyl.

2. The compound of claim 1, wherein $R^1$ is ethyl, isopropyl, iodo, ethynyl or cyclopropyl.

3. The compound of claim 2, wherein each $R^a$ is independently hydrogen, halo, alkyl, alkoxy, hydroxy, haloalkoxy, alkylsulfonyl or —C≡C—$R^b$—.

4. The compound of claim 3, wherein $R^7$ and $R^8$ are hydrogen.

5. The compound of claim 3, wherein one of $R^7$ and $R^8$ is hydrogen and the other is alkyl, hydroxyalkyl or haloalkyl.

6. The compound of claim 4, wherein $R^a$ is hydrogen, alkyl, alkoxy, hydroxy, halo, haloalkyl or haloalkoxy.

7. The compound of claim 5, wherein $R^a$ is hydrogen, alkyl or alkoxy.

8. A pharmaceutical composition comprising:
  (a) a pharmaceutically acceptable excipient; and
  (b) a compound of claim 1.

9. A method for treating, said method comprising administering to a subject in need thereof an effective amount of a compound of claim 1.

10. A method for treating asthma, said method comprising administering to a subject in need thereof an effective amount of a compound of claim 1.

* * * * *